(12) United States Patent
Shi et al.

(10) Patent No.: US 11,160,739 B1
(45) Date of Patent: Nov. 2, 2021

(54) COMPOSITIONS AND METHODS FOR ALTERING THE COLOR OF THE HAIR

(71) Applicant: L'Oreal, Paris (FR)

(72) Inventors: Minli Shi, Jersey City, NJ (US); Mohamad Amer Alkahwaji, Hoboken, NJ (US); Leslie A. Warner, Jersey City, NJ (US); Sarah Barrie Machover, New York, NY (US); Kimberly Christine Bogart Dreher, Brielle, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/915,365

(22) Filed: Jun. 29, 2020

(51) Int. Cl.
| | |
|---|---|
| *A61Q 5/10* | (2006.01) |
| *A61K 8/44* | (2006.01) |
| *A61K 8/40* | (2006.01) |
| *A61K 8/73* | (2006.01) |
| *A61K 8/365* | (2006.01) |
| *A61K 8/41* | (2006.01) |
| *A61K 8/92* | (2006.01) |

(52) U.S. Cl.
CPC .............. *A61K 8/447* (2013.01); *A61K 8/365* (2013.01); *A61K 8/40* (2013.01); *A61K 8/41* (2013.01); *A61K 8/731* (2013.01); *A61K 8/92* (2013.01); *A61Q 5/10* (2013.01); *A61K 2800/48* (2013.01)

(58) Field of Classification Search
CPC .......... A61Q 5/10; A61Q 5/065; A61K 8/342; A61K 8/41; A61K 2800/43; A61K 8/361; A61K 8/36; A61K 2800/432; A61K 31/13; A61K 8/447; A61K 8/365; A61K 8/731; A61K 8/92; A61K 2800/48

USPC .............................................................. 8/405
See application file for complete search history.

(56) References Cited

U.S. PATENT DOCUMENTS

| | | |
|---|---|---|
| 3,288,770 A | 11/1966 | Butler |
| 3,412,019 A | 11/1968 | Hoover et al. |
| 4,003,699 A | 1/1977 | Rose et al. |
| 4,137,180 A | 1/1979 | Naik et al. |
| RE30,199 E | 1/1980 | Rose et al. |
| 4,772,462 A | 9/1988 | Boothe et al. |
| 4,874,554 A | 10/1989 | Lange et al. |
| 5,061,289 A | 10/1991 | Clausen et al. |
| 5,380,340 A | 1/1995 | Neunhoeffer et al. |
| 5,534,267 A | 7/1996 | Neunhoeffer et al. |
| 5,663,366 A | 9/1997 | Neunhoeffer et al. |
| 5,708,151 A | 1/1998 | Möckli |

(Continued)

FOREIGN PATENT DOCUMENTS

| | | |
|---|---|---|
| DE | 2359399 A1 | 6/1975 |
| DE | 3843892 A1 | 6/1990 |

(Continued)

OTHER PUBLICATIONS

Copending As-filed U.S. Appl. No. 17/101,206, filed Nov. 23, 2020.

(Continued)

*Primary Examiner* — Eisa B Elhilo
(74) *Attorney, Agent, or Firm* — The Marbury Law Group, PLLC

(57) ABSTRACT

The present disclosure relates compositions and methods for altering the color of the hair, the compositions comprising at least one amino acid, at least one carboxylic acid, optionally at least one amine, and at least one hair coloring agent.

19 Claims, 2 Drawing Sheets

(56) References Cited

U.S. PATENT DOCUMENTS

| | | | |
|---|---|---|---|
| 5,766,576 A | 6/1998 | Löwe et al. | |
| 6,099,592 A | 8/2000 | Vidal et al. | |
| 6,284,003 B1 | 9/2001 | Rose et al. | |
| 6,730,789 B1 | 5/2004 | Birault et al. | |
| 8,236,063 B2 | 8/2012 | Reichert et al. | |
| 2004/0256598 A1* | 12/2004 | Plos | A61Q 5/10 252/299.01 |
| 2008/0317687 A1 | 12/2008 | Howe et al. | |
| 2010/0305064 A1 | 12/2010 | Walsh | |
| 2014/0246041 A1 | 9/2014 | Krueger | |
| 2014/0305464 A1* | 10/2014 | Degeorge | A61K 8/22 132/208 |
| 2014/0326270 A1* | 11/2014 | Degeorge | A45D 7/04 132/208 |
| 2015/0265525 A1* | 9/2015 | Benn | A61K 8/92 206/568 |
| 2015/0290093 A1* | 10/2015 | Salvemini | A61K 8/22 132/208 |
| 2018/0116942 A1* | 5/2018 | Mahadeshwar | A61K 8/817 |
| 2018/0177690 A1* | 6/2018 | Boulineau | A61K 8/365 |
| 2018/0353408 A1* | 12/2018 | Dreher | A45D 7/04 |
| 2018/0353409 A1* | 12/2018 | Dreher | A61K 8/362 |

FOREIGN PATENT DOCUMENTS

| | | |
|---|---|---|
| DE | 4133957 A1 | 4/1993 |
| DE | 19543988 A1 | 5/1997 |
| EP | 0080976 A1 | 6/1983 |
| EP | 0714954 A2 | 6/1996 |
| EP | 0770375 A1 | 5/1997 |
| FR | 2733749 A1 | 11/1996 |
| FR | 2801308 A1 | 5/2001 |
| GB | 1026978 A | 4/1966 |
| GB | 1153196 A | 5/1969 |
| JP | 02-019576 A | 1/1990 |
| JP | 05-163124 A | 6/1993 |
| WO | 94/08969 A1 | 4/1994 |
| WO | 94/08970 A1 | 4/1994 |
| WO | 95/01772 A1 | 1/1995 |
| WO | 95/15144 A1 | 6/1995 |
| WO | 96/15765 A1 | 5/1996 |
| WO | 2013/075892 A2 | 5/2013 |
| WO | 2014/020148 A1 | 2/2014 |
| WO | 2019/133785 A1 | 7/2019 |

OTHER PUBLICATIONS

Copending As-filed U.S. Appl. No. 17/133,376, filed Dec. 23, 2020.
Copending As-filed U.S. Appl. No. 17/132,697, filed Dec. 23, 2020.
Porter, M.R., "Handbook of Surfactants," published by Blackie & Son (Glasgow and London), 1991, pp. 116-178.
International Search Report and Written Opinion for counterpart Application No. PCT/US2020/067153, dated Apr. 29, 2021.

\* cited by examiner

COMPOSITIONS AND METHODS FOR ALTERING THE COLOR OF THE HAIR

TECHNICAL FIELD

The present disclosure generally relates to compositions and methods for altering the color of the hair.

BACKGROUND

It is known that consumers desire to use cosmetic and care compositions that enhance the appearance of keratinous substrates such as hair, e.g., by changing the color, style, and/or shape of the hair, and/or by imparting various properties to hair, such as shine and conditioning. Many of the known compositions and processes for enhancing the appearance of the hair involve chemical treatment of the hair. For example, the process of altering the color of hair can involve depositing an artificial color onto the hair which provides a different shade or color to the hair and/or lifting the color of the hair, such as lightening the color of dark hair to a lighter shade.

In general, hair-lightening or color-lifting compositions possess an alkalinity such that these compositions have a pH value above 7, typically pH 9 and above, and generally require the presence of an alkalizing agent in amounts sufficient to make such compositions alkaline. The alkalizing agent causes the hair shaft to swell, thus allowing an oxidizing agent to oxidize the melanin pigment, rendering the molecule colorless. This process is conventionally referred to as "bleaching" the hair.

Following a hair bleaching process, consumers typically also deposit color into or onto the bleached hair in order to obtain a hair color that is different than either the color of the hair prior to bleaching, or the color of the bleached hair. This process is conventionally referred to as "coloring" or "dyeing" the hair.

The most common hair dyeing processes are permanent and semi-permanent or temporary hair dyeing. Permanent hair dyeing compositions uses oxidation dye precursors, which are also known as primary intermediates or couplers. These oxidation dye precursors are colorless or weakly colored compounds which, when combined with oxidizing products, give rise to colored complexes by a process of oxidative condensation. The permanent hair dye compositions also contain ammonia or other alkalizing agents which causes the hair shaft to swell, thus allowing the small oxidative dye molecules to penetrate the cuticle and cortex before the oxidation condensation process is completed. The resulting larger-sized colored complexes from the oxidative reaction are then trapped inside the hair fiber, thereby permanently altering the color of the hair.

On the other hand, semi-permanent or temporary hair dyeing compositions typically use pigments, liposoluble dyes, or direct dyes chosen from acidic (anionic), basic (cationic), or neutral direct dyes which are deposited onto the hair fiber to impart color to the hair.

While the process of bleaching the hair followed by dyeing the hair is effective in altering the color of the hair, these chemical treatments are harsh and can damage the hair fibers, leading to decreased strength of the hair, as well as negatively affecting the sensorial properties of the hair, such as the smoothness, shine, and feel. Additionally, hair that is damaged during the bleaching and/or dyeing process may not take up color satisfactorily, resulting in unevenness or non-uniformity of color. Thus, in order to reduce or avoid these drawbacks, the use of new and additional components for use with the processes for altering the color of the hair is needed.

However, the choice of such components could pose difficulties insofar as they cannot be detrimental to other cosmetic attributes such as ease and uniformity of application, rheology or viscosity properties of the compositions, stability of the compositions, or color deposit and target shade formation, and they cannot result in more disadvantages such as increased damage or a less healthy look to the hair. It is therefore desirable to provide the consumer with compositions and methods that can alter the color of the hair in an effective manner, while providing other cosmetic advantages such as shine, conditioning, fiber strength, and/ or a healthy appearance to the hair, while avoiding or minimizing damage to the hair.

SUMMARY

It has now been found that the addition of a combination of one or more amino acids, one or more carboxylic acids, and optionally one or more amines to hair dyeing compositions results in surprisingly and unexpectedly beneficial properties, such as improved evenness of color, improved hair strength, and improved hair feel. Surprisingly and unexpectedly, the compositions have been found to impart increased strength to the hair, while providing uniform color and mitigating color shift. The disclosure therefore relates to compositions and methods for imparting color to the hair, the compositions comprising at least one amino acid, at least one carboxylic acid, optionally at least one amine, and at least one hair coloring agent.

In one embodiment, the disclosure relates to hair color compositions comprising (a) at least one amino acid, (b) at least one carboxylic acid, (c) optionally at least one amine, and (d) at least one hair coloring agent chosen from direct dyes and pigments, wherein the composition has a pH ranging from about 2 to less than 7.

In a further embodiment, the disclosure relates to methods of altering the color of the hair, the methods comprising applying to the hair a composition comprising (a) at least one amino acid, (b) at least one carboxylic acid, (c) optionally at least one amine, and (d) at least one hair coloring agent chosen from direct dyes and pigments, wherein the composition has a pH ranging from about 2 to less than 7.

In a still further embodiment, the disclosure relates to hair color compositions comprising (a) from about 0.2% to about 5% taurine, (b) from about 0.2% to about 5% citric acid, (c) from about 0.01% to about 5% of at least one amine, (d) at least one cationic surfactant, (e) at least one fatty alcohol, and (f) at least one hair coloring agent selected from direct dyes, wherein the composition has a pH ranging from about 3 to about 4.

DETAILED DESCRIPTION

Figure 1:
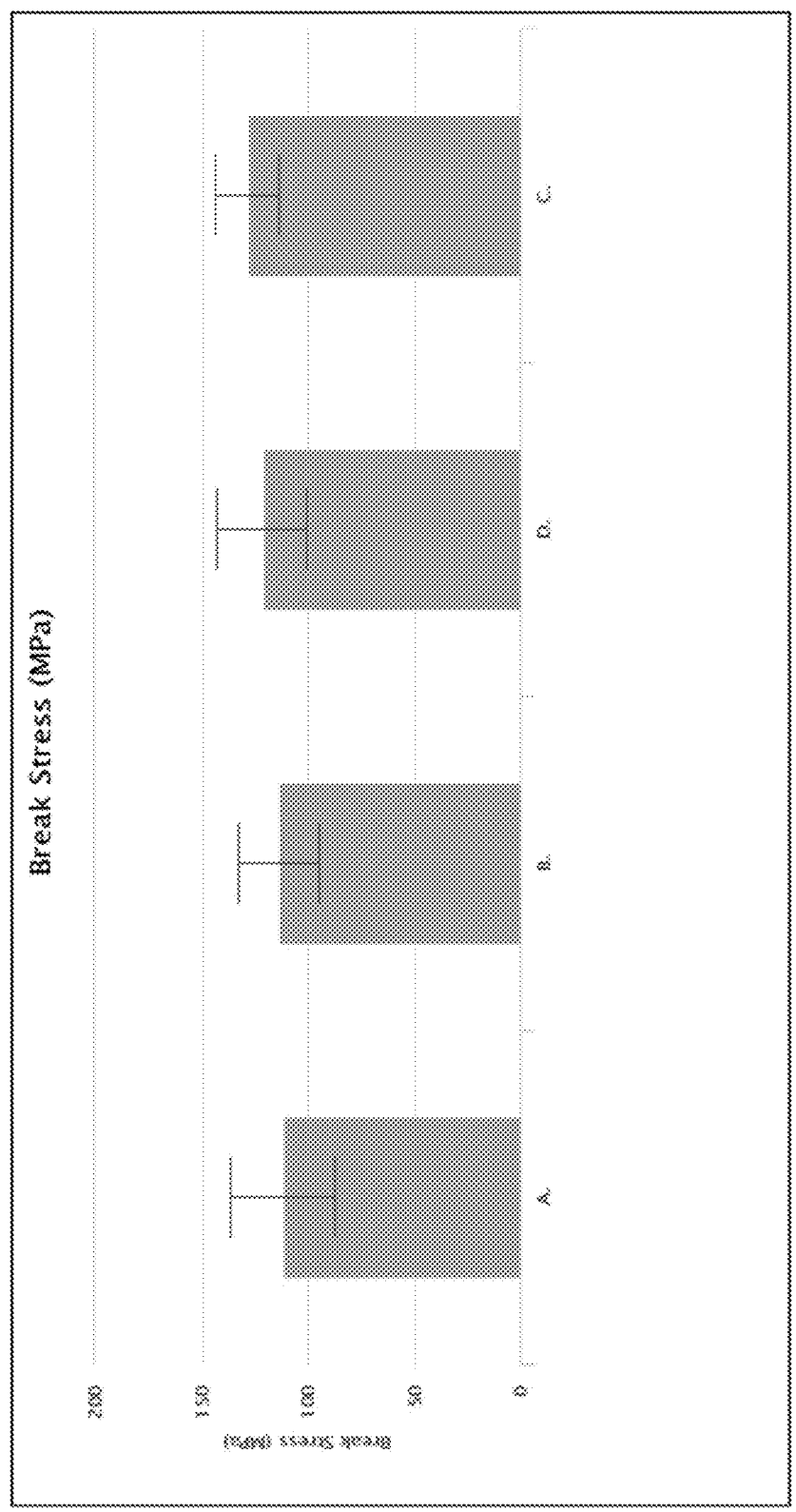
FIG. 1 is a comparison of Break Stress of hair.

The disclosure relates to compositions and methods for altering the color of the hair. Hair color compositions according to the disclosure surprisingly and unexpectedly provide benefits such as improved strength, smoothness, and softness to the hair, while also reducing color shift and providing improved uniformity or evenness of color. The hair color compositions are also surprisingly stable. The methods comprise applying hair color compositions according to the disclosure to the hair.

Compositions

The hair color compositions comprise at least one amino acid, at least one carboxylic acid, optionally at least one amine, and at least one hair coloring agent. The hair coloring compositions may be in any suitable form, such as, for example, an emulsion or a gel.

Amino Acid

The hair color compositions according to the disclosure comprise at least one amino acid. As used herein, the term "amino acid" includes amino acids such as proteinogenic amino acids, amino sulfonic acids, and salts thereof.

Amino acids are simple organic compounds containing both a carboxylic acid group (—COOH) and an amino group (—NH$_2$). Amino sulfonic acids are simple organic compounds containing both a sulfonic acid group (—SO$_2$OH) and an amino group (—NH$_2$). Accordingly, amino acids useful according to the disclosure may, in certain embodiments, be selected from compounds of formula (I) and formula (II):

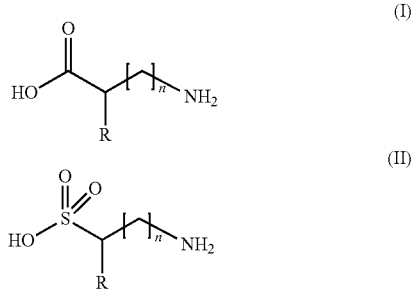

wherein:
R represents a hydrogen atom, a linear or branched, preferably linear, C$_1$-C$_5$ alkyl group, said alkyl group being optionally substituted with at least one group chosen from hydroxyl, —C(O)—OH, —S(O)$_2$—OH, —C(O)—O$^-$ and M$^+$, and S(O)$_2$—O$^-$ and M$^+$, with M$^+$ representing a cationic counter-ion such as an alkali metal, alkaline earth metal, or ammonium, and
n is 0 or 1.

The amino acids may be in their non-ionized form (I) and (II), or in their ionized or betaine form (I') and (II'):

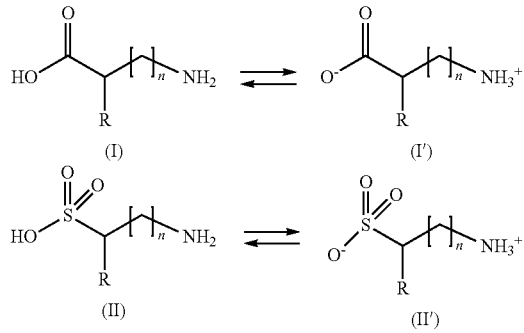

wherein R and n are as defined above.

The one or more amino acids may also be in their conjugate base form (Ib) and (IIb):

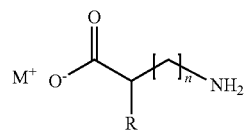

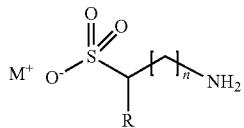

wherein R and n are as defined above.

Well-known amino acids include the twenty amino acids that form the proteins of living organisms (standard proteinogenic amino acids): alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine. The amino acids of the instant disclosure, however, are not limited to the standard proteinogenic amino acids.

Non-limiting examples of amino sulfonic acids include aminomethane sulfonic acid, 2-aminoethane sulfonic acid (taurine), aminopropane sulfonic acid, aminobutane sulfonic acid, aminohexane sulfonic acid, aminoisopropyl sulfonic acid, aminododecyl sulfonic acid, aminobenzene sulfonic acid, aminotoulene sulfonic acid, sulfanilic acid, chlorosulfanilic acid, diamino benzene sulfonic acid, amino phenol sulfonic acid, amino propyl benzene sulfonic acid, amino hexyl benzene sulfonic acid, and a mixture thereof.

In some cases, charged amino acids may be used. Non-limiting examples of charged amino acids include arginine, lysine, aspartic acid, and glutamic acid. In some cases, polar amino acids are useful. Non-limiting examples of polar amino acids include glutamine, asparagine, histidine, serine, threonine, tyrosine, cysteine, methionine, and tryptophan.

In some cases, hydrophobic amino acids may be employed. Non-limiting examples of hydrophobic amino acids include alanine, isoleucine, leucine, phenylalanine, valine, proline, and glycine.

In certain exemplary embodiments, compositions according to the disclosure include at least one amino acid selected from the group consisting of glycine, alanine, serine, beta-alanine, taurine, sodium glycinate, sodium alaninate, sodium serinate, lithium beta-alanine, sodium taurate, or combinations thereof.

In further exemplary embodiments, compositions according to the disclosure include only amino acids, for example, those selected from the group consisting of aspartic acid, cysteine, glycine, lysine, methionine, proline, tyrosine, phenylalanine, carnitine, taurine, or a salt thereof.

In one exemplary embodiment, the compositions include at least taurine. In a further embodiment, the only amino acid in the composition is taurine.

The total amount of the at least one amino acid may range from about 0.01% to about 10% by weight, relative to the total weight of the hair color composition. For example, in some embodiments, the total amount of the at least one amino acid may range from about 0.05% to about 5%, such as about 0.1% to about 5%, about 0.1% to about 4%, about 0.1% to about 3%, about 0.1% to about 2.5%, about 0.1% to about 2%, about 0.1% to about 1.5%, about 0.1% to about 1%, or about 0.1% to about 0.5% by weight, relative to the total weight of the hair color composition. In other embodiments, the total amount of the at least one amino acid ranges from about 0.2% to about 5%, about 0.2% to about 4%, about 0.2% to about 3%, about 0.2% to about 2.5%, about 0.2% to about 2%, about 0.2% to about 1.5%, about 0.2% to about 1%, about 0.5% to about 5%, about 0.5% to about 4%, about 0.5% to about 3%, about 0.5% to about 2.5%, about 0.5% to about 2%, about 0.5% to about 1.5%, or about 0.5% to about 1% by weight, relative to the total weight of the hair color composition. In still further embodiments, the at least one amino acid may be present in an amount ranging from about 1% to about 5%, about 1% to about 4.5%, about 1% to about 4%, about 1% to about 3.5%, about 1% to about 3%, about 1% to about 2.5%, about 1% to about 2%, about 1.5% to about 5%, about 1.5% to about 4.5%, about 1.5% to about 4%, about 1.5% to about 3.5%, about 1.5% to about 3%, about 1.5% to about 2.5%, about 1.5% to about 2%, about 2% to about 5%, about 2% to about 4.5%, about 2% to about 4%, about 2% to about 3.5%, about 2% to about 3%, or about 2% to about 2.5% by weight, relative to the total weight of the hair color composition.

The total amount of the at least one amino acid may, in certain embodiments, be about 0.5%, about 1%, about 1.5%, about 2%, about 2.5%, about 3%, about 3.5%, about 4%, about 4.5%, or about 5% by weight, relative to the total weight of the hair color composition. It is to be understood that any of the above-recited numbers may provide an upper or lower boundary for a range of the total amount of the at least one amino acid.

For example, in one non-limiting embodiment, the hair color compositions comprise taurine in an amount ranging from about 0.2% to about 5%.

Carboxylic Acid

The hair color compositions include at least one carboxylic acid. As used herein, the term "carboxylic acid" includes salts of carboxylic acids. In certain embodiments, the carboxylic acids include non-polymeric mono, di, and/or tricarboxylic acid which are organic compounds having one (mono), two (di), or three (tri) carboxylic acid groups (—COOH). The non-polymeric mono-, di-, and tri-carboxylic acids, and/or salts thereof, may have a molecular weight of less than about 500 g/mol, less than about 400 g/mol, or less than about 300 g/mol.

Non-limiting examples of mono-carboxylic acids, or salts thereof, include formic acid, acetic acid, propionic acid, butyric acid, valeric acid, caproic acid, entanthic acid, caprylic acid, pelargonic acid, capric acid, undecylic acid, lauric acid, tridecylic acid, lauric acid, tridecylic acid, myristic acid, pentadecylic acid, palmitic acid, margaric acid, stearic acid, nonadecylic acid, arachidic acid, lactic acid, a salt thereof, and mixtures thereof.

Non-limiting examples of di-carboxylic acids and/or salts thereof include oxalic acid, malonic acid, malic acid, glutaric acid, citraconic acid, succinic acid, adipic acid, tartaric acid, fumaric acid, maleic acid, sebacic acid, azelaic acid, dodecanedioic acid, phthalic acid, isophthalic acid, terephthalic acid, 2,6-naphthalene dicarboxylic acid, a salt thereof, and a mixture thereof. In some cases, the hair color compositions include oxalic acid, malonic acid, malic acid, maleic acid, a salt thereof, and mixtures thereof.

Non-limiting examples of tricarboxylic acids and salts thereof include citric acid, isocitric acid, aconitric acid, propane-1,2,3-tricarboxylic acid, benzene-1,3,5-tricarboxylic acid, a salt thereof, and a mixture thereof. In some instances, the hair color compositions include at least citric acid and/or a salt thereof.

In one or more embodiments, the hair color composition comprises at least one carboxylic acid selected from the group consisting of oxalic acid, malonic acid, glutaric acid, succinic acid, adipic acid, glycolic acid, citric acid, tartaric acid, malic acid, sebacic acid, maleic acid, fumaric acid, benzoic acid, citraconic acid, aconitic acid, propane-1,2,3-tricarboxylic acid, trimesic acid, or combinations thereof.

In one exemplary embodiment, the compositions include at least citric acid. In a further embodiment, the only carboxylic acid in the composition is citric acid.

The total amount of the at least one carboxylic acid may range from about 0.01% to about 10% by weight, relative to the total weight of the hair color composition. For example, in some embodiments, the total amount of the at least one carboxylic acid may range from about 0.05% to about 5%, such as about 0.1% to about 5%, about 0.1% to about 4%, about 0.1% to about 3%, about 0.1% to about 2.5%, about 0.1% to about 2%, about 0.1% to about 1.5%, about 0.1% to about 1%, about 0.2% to about 5%, about 0.2% to about 4%, about 0.2% to about 3%, about 0.2% to about 2.5%, about 0.2% to about 2%, about 0.2% to about 1.5%, about 0.2% to about 1%, about 0.5% to about 5%, about 0.5% to about 4%, about 0.5% to about 3%, about 0.5% to about 2.5%, about 0.5% to about 2%, about 0.5% to about 1.5%, about 0.5% to about 1%, or about 0.1% to about 0.5% by weight, relative to the total weight of the hair color composition. In other embodiments, the total amount of the at least one carboxylic acid ranges from about 0.5% to about 5%, about 0.5% to about 4%, about 0.5% to about 3%, about 0.5% to about 2.5%, about 0.5% to about 2%, about 0.5% to about 1.5%, or about 0.5% to about 1% by weight, relative to the total weight of the hair color composition. In still further embodiments, the at least one carboxylic acid may be present in an amount ranging from about 1% to about 5%, about 1% to about 4.5%, about 1% to about 4%, about 1% to about 3.5%, about 1% to about 3%, about 1% to about 2.5%, about 1% to about 2%, about 1.5% to about 5%, about 1.5% to about 4.5%, about 1.5% to about 4%, about 1.5% to about 3.5%, about 1.5% to about 3%, about 1.5% to about 2.5%, about 1.5% to about 2%, about 2% to about 5%, about 2% to about 4.5%, about 2% to about 4%, about 2% to about 3.5%, about 2% to about 3%, about 2% to about 2.5%, about 2.5% to about 5%, about 2.5% to about 4.5%, about 2.5% to about 4%, about 2.5% to about 3.5%, or about 2.5% to about 3% by weight, relative to the total weight of the hair color composition.

The total amount of the at least one carboxylic acid may, in certain embodiments, be about 0.5%, about 1%, about 1.5%, about 2%, about 2.5%, about 3%, about 3.5%, about 4%, about 4.5%, or about 5% by weight, relative to the total weight of the hair color composition. It is to be understood that any of the above-recited numbers may provide an upper or lower boundary for a range of the total amount of the at least one carboxylic acid.

For example, in one non-limiting embodiment, the hair color compositions comprise citric acid in an amount ranging from about 0.2% to about 5%.

In certain embodiments, it may be particularly useful to choose an amount of carboxylic acid(s) and amino acid(s) in a ratio of approximately 1:1, such as 1.1:1, 1.2:1, 1.3:1, 1.4:1, 1.5:1, 1:1.1, 1:1.2, 1:1.3, 1:1.4, or 1:1.5 as carboxylic acid(s):amino acid(s).

Amine

The hair color compositions according to the disclosure may optionally comprise at least one amine.

Non-limiting examples of the at least one amine include monoethanolamine (also known as ethanolamine or MEA), diethanolamine, triethanolamine, monoisopropanolamine, diisopropanolamine, triisopropanol amine, dimethylstearylamine, N-dimethylaminoethanolamine, 2-amino-2-methyl- 1-propanol, 2-amino-2-methyl-1,3-propanediol, 3-amino-1,2-propanediol, tris(hydroxymethylamino)methane, 1,3-diamino-propane, 1,3-diamino-2-propanol, and mixtures thereof. Preferably, the amine is MEA.

If present, the at least one amine may be present in the composition in an amount up to about 10%, such from about 0.001% up to about 10%, or from about 0.01% up to about 5%, up to about 4%, up to about 3.9%, up to about 3.8%, up to about 3.7%, up to about 3.6%, up to about 3.5%, up to about 3.4%, up to about 3.3%, up to about 3.2%, up to about 3.1%, up to about 3%, up to about 2.9%, up to about 2.8%, up to about 2.7%, up to about 2.6%, up to about 2.5%, up to about 2.4%, up to about 2.3%, up to about 2.2%, up to about 2.1%, up to about 2.0%, up to about 1.9%, up to about 1.8%, up to about 1.7%, up to about 1.6%, up to about 1.5%, up to about 1.4%, up to about 1.3%, up to about 1.2%, up to about 1.1%, up to about 1%, up to about 0.9%, up to about 0.8%, up to about 0.7%, up to about 0.6%, up to about 0.5%, up to about 0.4%, up to about 0.3%, up to about 0.2%, up to about 0.1%, or up to about 0.05% by weight, based on the weight of the composition. By way of example, the at least one amine may be present in an amount ranging from about 0.1% to about 5%, such as from about 0.01% to about 5%, about 0.01% to about 4.5%, about 0.01% to about 4%, about 0.01% to about 3.5%, about 0.01% to about 3%, about 0.01% to about 2.5%, about 0.01% to about 2%, about 0.01% to about 1.5%, about 0.01% to about 1%, about 0.1% to about 5%, about 0.1% to about 4.5%, about 0.1% to about 4%, about 0.05% to about 3.5%, about 0.05% to about 3%, about 0.05% to about 2.5%, about 0.05% to about 2%, about 0.05% to about 1.5%, about 0.05% to about 1%, about 0.1% to about 5%, about 0.1% to about 4.5%, about 0.1% to about 4%, about 0.1% to about 3.5%, about 0.1% to about 3%, about 0.1% to about 2.5%, about 0.1% to about 2%, about 0.1% to about 1.5%, about 0.1% to about 1%, or an amount of about 0.1%, about 0.2%, about 0.3%, about 0.4%, about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, about 2%, about 2.5%, about 3%, about 3.5%, about 4%, about 4.5%, or about 5% by weight, based on the weight of the composition.

For example, in one non-limiting embodiment, the hair color compositions comprise monoethanolamine in an amount ranging from about 0.1% to about 5%.

Fatty Alcohol

The hair color compositions according to the disclosure optionally comprise at least one fatty alcohol. In certain embodiments, the compositions comprise at least two fatty alcohols. As used herein, "fatty alcohol" refers to any alcohol with a carbon chain of C5 or greater, such as, for example, C8 or greater, C10 or greater, and C12 or greater.

The fatty alcohols useful according to the disclosure include, but are not limited to, alkoxylated or non-alkoxylated, saturated or unsaturated, linear or branched, fatty alcohols, for example with from 6 to 30 carbon atoms, such as from 8 to 30 carbon atoms.

The at least one fatty alcohol may be chosen from, for example, C9-C11 alcohols, C12-C13 alcohols, C12-C15 alcohols, C12-C16 alcohols, C14-C15 alcohols, C12-C22 alcohols, arachidyl alcohol, behenyl alcohol, caprylic alcohol, cetearyl alcohol, cetyl alcohol, coconut alcohol, decyl alcohol, hydrogenated tallow alcohol, jojoba alcohol, lauryl alcohol, myristyl alcohol, oleyl alcohol, palm alcohol, palm kernel alcohol, stearyl alcohol, tallow alcohol, tridecyl alcohol, or a mixture thereof. For example, cetyl alcohol, stearyl alcohol and their mixture (cetylstearyl alcohol), octyldodecanol, 2-butyloctanol, 2-hexyldecanol, 2-undecylpentadecanol, oleic alcohol, linoleic alcohol, or mixtures thereof may be particularly chosen.

As used herein, "alkoxylated fatty alcohol" refers to any fatty alcohol with a carbon chain of C5 or greater, as defined above, further comprising at least one alkoxy group. For example, the at least one alkoxylated fatty alcohol may have a carbon chain of C8 or greater, C10 or greater, and C12 or greater. Further, for example, the at least one alkoxylated fatty alcohol may be chosen from alkoxylated polymers (including co-, ter-, and homo-polymers) derived from alcohols such as glycerol (e.g. polyglyceryl derived from four glycerol molecules). The at least one alkoxy group of the at least one alkoxylated fatty alcohol may, for example, be derived from an alkoxylation reaction carried out with alkylene oxide. Non-limiting examples of at least one alkoxylated fatty alcohol include any fatty alcohol comprising at least one polyethylene glycol ether and any fatty alcohol comprising at least one polypropylene glycol ether.

By way of example, ceteareth-2, ceteareth-3, ceteareth-4, ceteareth-5, ceteareth-6, ceteareth-7, ceteareth-8, ceteareth-9, ceteareth-10, ceteareth-11, ceteareth-12, ceteareth-13, ceteareth-14, ceteareth-15, ceteareth-16, ceteareth-17, ceteareth-18, ceteareth-20, ceteareth-22, ceteareth-23, ceteareth-24, ceteareth-25, ceteareth-27, ceteareth-28, ceteareth-29, ceteareth-30, ceterarel:h-33, ceteareth-34, ceteareth-40, ceteareth-50, ceteareth-55, ceteareth-60, ceteareth-80, ceteareth-100, laureth-1, laureth-2, laureth-3, laureth-4, laureth-5, laureth-6, laureth-7, laureth-8, laureth-9, laureth-10, laureth-11, laureth-12, laureth-13, laureth-14, laureth-15, lauretih-16, laureth-20, laureth-23, laureth-25, laureth-30, laureth-40, deceth-3, deceth-5, oleth-5, oleth-30, steareth-2, steareth-10, steareth-20, steareth-100, cetylsteareth-12, ceteareth-5, ceteareth-5, polyglyceryl 4-lauryl ether, polyglyceryl 4-oleyl ether, polyglyceryl 2-oleyl ether, polyglyceryl 2-cetyl ether, polyglyceryl 6-cetyl ether, polyglyceryl 6-oleylcetyl ether, polyglyceryl 6-octadecyl ether, C9-C11 pareth-3, C9-C11 pareth-6, C11-C15 pareth-3, C11-C15 pareth-5, C11-C15 pareth-12, C11-C15 pareth-20, C12-C15 pareth-9, C12-C15 pareth-12, C22-C24 pareth-33, and mixtures thereof may be chosen.

If present, the total amount of the at least one fatty alcohol in the composition may range up to about 10%, such from about 0.01% up to about 10%, from about 0.1% up to about 10%, or from about 1% up to about 10% by weight, based on the total weight of the composition. By way of non-limiting example, the at least one fatty alcohol may be present in an amount up to about 9%, up to about 8%, up to about 7%, up to about 6%, up to about 5%, up to about 4%, up to about 3%, up to about 2%, or up to about 1% by weight, based on the weight of the composition. In further embodiments, the at least one fatty alcohol may be present in an amount ranging from about 1% to about 9%, about 1% to about 8%, about 1% to about 7%, about 1% to about 6%, about 1% to about 5%, about 1% to about 4%, about 1% to about 3%, about 1% to about 2%, about 2% to about 10%, about 2% to about 9%, about 2% to about 8%, about 2% to about 7%, about 2% to about 6%, about 2% to about 5%, about 2% to about 4%, about 2% to about 3%, about 3% to about 10%, about 3% to about 9%, about 3% to about 8%, about 3% to about 7%, about 3% to about 6%, about 3% to about 5%, about 3% to about 4%, about 4% to about 10%, about 4% to about 9%, about 4% to about 8%, about 4% to about 7%, about 4% to about 6%, about 4% to about 5%, about 5% to about 10%, about 5% to about 9%, about 5% to about 8%, about 5% to about 7%, or about 5% to about 6% by weight, based on the weight of the composition.

Surfactants

The hair color compositions optionally comprise one or more surfactants selected from cationic surfactants, anionic surfactants, nonionic surfactants, amphoteric surfactants, and mixtures thereof.

The total amount of the one or more surfactants included in the hair color compositions can vary, especially depending on the type of hair color composition in with they are contained. If present, the total amount of the one or more surfactants typically ranges from about 0.01% to about 10% by weight, relative to the total weight of the hair color composition, including all ranges and subranges therebetween. In some cases, the total amount of the one or more surfactants ranges from about 0.1% to about 10%, about 0.1% to about 9%, about 0.1% to about 8%, about 0.1% to about 7%, about 0.1% to about 6%, about 0.1% to about 5%, about 0.1% to about 4%, about 0.1% to about 3%, about 0.1% to about 2%, about 0.5% to about 10%, about 0.5% to about 9%, about 0.5% to about 8%, about 0.5% to about 7%, about 0.5% to about 6%, about 0.5% to about 5%, about 0.5% to about 4%, about 0.5% to about 3%, about 0.5% to about 2%, 1% to about 10%, about 1% to about 9%, about 1% to about 8%, about 1% to about 7%, about 1% to about 6%, about 1% to about 5%, about 1% to about 4%, about 1% to about 3%, or about 1% to about 2% by weight, relative to the total weight of the hair treatment composition.

Cationic Surfactants

The hair color compositions may optionally comprise one or more cationic surfactants. The term "cationic surfactant" means a surfactant comprising, as ionic or ionizable groups, only cationic groups. Non-limiting examples of cationic surfactants that may be used include polyoxyalkylenated primary, secondary, or tertiary fatty amine salts, quaternary ammonium salts, and mixtures thereof.

As quaternary ammonium salts, quaternary ammonium salts of formula (III) may be chosen:

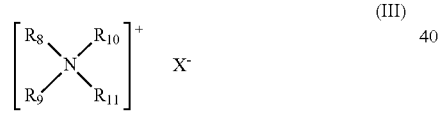

(III)

wherein:
groups R8 to R11 are independently chosen from linear or branched aliphatic groups containing from 1 to 30 carbon atoms, or an aromatic group such as aryl or alkylaryl, at least one of the groups R8 to R11 including from 8 to 30 carbon atoms, such as from 12 to 24 carbon atoms, it being possible for the linear or branched aliphatic groups to include heteroatoms such as, for example, oxygen, nitrogen, and/or sulfur, these heteroatoms not being adjacent, and halogens; and X$^-$ is an anion chosen from the group consisting of halides such as bromides, chlorides, iodides, fluorides, phosphates, acetates, lactates, (C1-C4)alkyl sulfates, (C1-C4)alkyl sulfonates or (C1-C4)alkylaryl sulfonates; C1-C30 alkyl, C1-C30 alkoxy, (C2-C6)polyoxyalkylene, C1-C30 alkylamide, (C12-C22)alkyl-(C2C6) alkylamido, (C12-C22)alkyl acetate, and C1-C30 hydroxyalkyl groups.

Mention may be made as exemplary embodiments of formula (III) of tetraalkylammonium halides, such as chlorides, for example dialkyldimethylammonium or alkyltrimethylammonium chlorides in which the alkyl group comprises from 12 to 22 carbon atoms, such as from 14 to 20 carbon atoms. By way of example, behenyltrimethylammonium chloride (behentrimonium chloride), distearyl-dimethylammonium chloride, cetyltrimethylammonium chloride (cetrimonium chloride), or benzyldimethylstearylammonium chloride may be chosen.

Mention may also be made of palmitylamidopropyltrimethylammonium or stearamidopropyldimethyl-(myristyl acetate)-ammonium halides, such as chlorides, for example the product sold under the name Ceraphyl® 70 by the company Van Dyk.

In certain embodiments, cationic surfactants of formula (III) are preferably chosen from alkyltrimethylammonium halides whose alkyl group includes from 12 to 22 carbon atoms, such as from 14 to 20 carbon atoms, may be chosen. For example, alkyltrimethylammonium chlorides, such as behenyltrimethylammonium chloride and cetyltrimethylammonium chloride, may be particularly useful.

In further embodiments, quaternary ammonium salts of imidazoline of formula (IV) may be chosen:

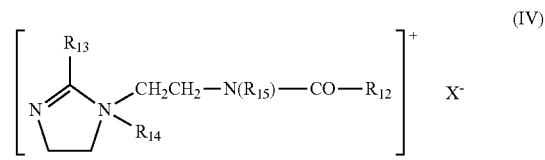

(IV)

wherein:
R12 represents an alkenyl or alkyl group comprising from 8 to 30 carbon atoms, for example derived from tallow fatty acids,
R13 represents a hydrogen atom, a C1-C4 alkyl group or an alkenyl or alkyl group comprising from 8 to 30 carbon atoms,
R14 represents a C1-C4 alkyl group,
R15 represents a hydrogen atom or a C1-C4 alkyl group, and
X$^-$ is an anion chosen from the group consisting of halides, phosphates, acetates, lactates, (C1-C4)alkyl sulfates, and (C1-C4)alkyl- or (C1-C4)alkylarylsulfonates.

In one exemplary embodiment of formula (IV), R12 and R13 denote a mixture of alkenyl or alkyl groups comprising from 12 to 21 carbon atoms, for example derived from tallow fatty acids, R14 denotes a methyl group, and R15 denotes a hydrogen atom. Such a product is sold, for example, under the name Rewoquat® W75 or W90 by the company Evonik.

In yet further embodiments, di- or triquaternary ammonium salts of formula (V) may be chosen:

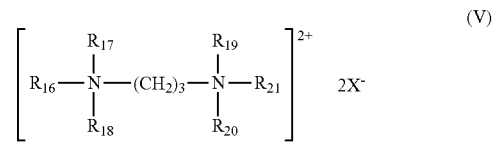

(V)

wherein:
R16 represents an alkyl group comprising from 16 to 30 carbon atoms, which is optionally hydroxylated and/or optionally interrupted with one or more oxygen atoms,
R17 represents hydrogen, an alkyl group comprising from 1 to 4 carbon atoms, or a group —(CH2)3-N$^+$(R16a)(R17a)(R18a), R16a, R17a and R18a, which may be identical or different, represent hydrogen or an alkyl group comprising from 1 to 4 carbon atoms, R18, R19, R20, and R21, which may be identical or different, represent hydrogen or an alkyl group comprising from 1 to 4 carbon atoms, and $X^-$ is an anion chosen from the group consisting of halides, acetates, phosphates, nitrates, (C1-C4)alkyl sulfates, and (C1-C4)alkyl- and (C1-C4)alkylarylsulfonates, for example methyl sulfate or ethyl sulfate.

Such compounds are, for example, Finquat CT-P (Quaternium 89) and Finquat CT (Quaternium 75), sold by the company Finetex.

In still further embodiments, quaternary ammonium salts containing one or more ester functions, such as those of formula (VI) may be chosen:

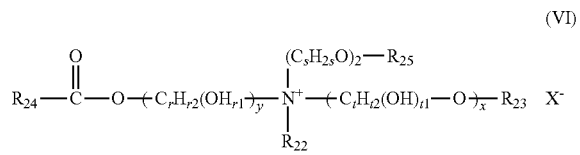

wherein:
R22 is chosen from C1-C6 alkyl groups and C1-C6 hydroxyalkyl or dihydroxyalkyl groups, R23 is chosen from the group $R_{26}-C(=O)-$; linear or branched, saturated or unsaturated C1-C22 hydrocarbon-based groups; and a hydrogen atom, R25 is chosen from the group $R_{28}-C(=O)-$; linear or branched, saturated or unsaturated C1-C6 hydrocarbon-based groups; and a hydrogen atom, R24, R26 and R28, which may be identical or different, are chosen from saturated or unsaturated, linear or branched C7-C21 hydrocarbon-based groups, r, s and t, which may be identical or different, are integers ranging from 2 to 6, r1 and t1, which may be identical or different, are equal to 0 or 1, y is an integer ranging from 1 to 10, x and z, which may be identical or different, are integers ranging from 0 to 10, X— is an anion, it being understood that r2+r1=2r and t1+t2=2t, and that the sum x+y+z ranges from 1 to 15, with the proviso that when x=0 then R23 is chosen from C1-C22 hydrocarbon-based groups, and that when z=0 then R25 denotes a linear or branched, saturated or unsaturated C1-C6 hydrocarbon-based group.

In exemplary embodiments of formula (VI), the alkyl groups R22 may be linear or branched, and are preferably linear. Preferably, R22 denotes a methyl, ethyl, hydroxyethyl or dihydroxypropyl group, and more particularly a methyl or ethyl group. Advantageously, the sum x+y+z ranges from 1 to 10. When R23 is a C1-C22 hydrocarbon-based groups, it may preferably comprise either from 12 to 22 carbon atoms or from 1 to 3 carbon atoms. Advantageously, R24, R26 and R28, which may be identical or different, are chosen from linear or branched, saturated or unsaturated C11-C21 hydrocarbon-based groups, and more particularly from linear or branched C11-C21 alkyl and alkenyl groups. Preferably, x and z, which may be identical or different, are equal to 0 or 1. Optionally, y is equal to 1. Preferably, r, s, and t, which may be identical or different, are equal to 2 or 3, and optionally are equal to 2.

The anion $X^-$ is preferably a halide, optionally chloride, bromide, or iodide, a (C1-C4)alkyl sulfate, a (C1-C4)alkylsulfonate, or a (C1-C4)alkylarylsulfonate, a methanesulfonate, a phosphate, a nitrate, a tosylate, an anion derived from an organic acid such as an acetate or a lactate, or any other anion that is compatible with the ammonium bearing an ester function. The anion X— is more particularly a chloride, a methyl sulfate, or an ethyl sulfate.

For example, the ammonium salts of formula (VI) in which R22 denotes a methyl or ethyl group, x and y are equal to 1, z is equal to 0 or 1, r, s and t are equal to 2, R23 is chosen from the group $R_{26}-C(=O)-$, methyl, ethyl, or C14-C22 hydrocarbon-based groups; and a hydrogen atom, R25 is chosen from the group $R_{28}-C(=O)-$; and a hydrogen atom, R24, R26 and R28, which may be identical or different, are chosen from linear or branched, saturated or unsaturated C13-C17 hydrocarbon-based groups, and preferably from linear or branched, saturated or unsaturated C13-C17 alkyl and alkenyl groups, may be chosen. Advantageously, the hydrocarbon-based groups are linear.

Among the compounds having formula (VI), mention may be made of salts, especially the chloride or methyl sulfate salts, of diacyloxyethyldimethylammonium, diacyloxyethylhydroxyethylmethylammonium, monoacyloxyethyldihydroxyethylmethyl-ammonium, triacyloxyethylmethylammonium or monoacyloxyethylhydroxyethyldimethylammonium, and mixtures thereof. The acyl groups preferably contain 14 to 18 carbon atoms and are obtained more particularly from a plant oil such as palm oil or sunflower oil. When the compound contains several acyl groups, these groups may be identical or different.

These products are obtained, for example, by direct esterification of triethanolamine, triisopropanolamine, alkyldiethanolamine or alkyldiisopropanolamine, which are optionally oxyalkylenated, with fatty acids or with fatty acid mixtures especially of plant or animal origin, or by transesterification of the methyl esters thereof. This esterification may be followed by a quaternization by means of an alkylating agent such as an alkyl halide, preferably methyl or ethyl halide, a dialkyl sulfate, preferably dimethyl or diethyl sulfate, methyl methanesulfonate, methyl para-toluenesulfonate, glycol chlorohydrin or glycerol chlorohydrin. Such compounds are sold, for example, under the names Dehyquart® by the company Henkel, Stepanquat® by the company Stepan, Noxamium® by the company CECA or Rewoquat® WE 18 by the company Evonik.

The one or more cationic surfactants may be chosen from, for example, a mixture of quaternary ammonium monoester, diester and triester salts with a weight majority of diester salts. Use may also be made of the ammonium salts containing at least one ester functional group that are described in U.S. Pat. Nos. 4,874,554 and 4,137,180. Use may also be made of behenoylhydroxypropyl-trimethylammonium chloride, for example, sold by the company Kao under the name Quartamin BTC 131. Preferably, the ammonium salts containing at least one ester function contain two ester functions.

Preferably, cationic surfactants used according to the invention are chosen from those having formula (III), among alkyltrimethylammonium salts whose alkyl group includes from 12 to 22 carbon atoms, such as from 14 to 20 carbon atoms, are chosen. For example, behenyltrimethylammonium salts, cetrimonium salts, or mixtures thereof, such as cetyltrimethylammonium chloride, behenyltrimethylammonium chloride, or mixtures thereof, may be used.

Anionic Surfactants

The hair color compositions may optionally include one or more anionic surfactants. The term "anionic surfactant" means a surfactant comprising, as ionic or ionizable groups, only anionic groups. These anionic groups may optionally be chosen from the groups $CO_2H$, $CO_2^-$, $SO_3H$, $SO_3^-$, $OSO_3H$, $OSO_3^-$ $O_2PO_2H$, $O_2PO_2H$ and $O_2PO_2^{2-}$.

Non-limiting examples of anionic surfactants include alkyl sulfates, alkyl ether sulfates, acyl isethionates, acyl glycinates, acyl taurates, acyl amino acids, acyl sarcosinates, sulfosuccinates, sulfonates, and a mixture thereof, wherein the alkyl and acyl groups of all these compounds comprise from 6 to 24 carbon atoms. In some cases, anionic sulfate surfactants may be excluded from the one or more anionic surfactants. In such cases, the one or more anionic surfactants may be selected from the group consisting of acyl isethionates, acyl glycinates, acyl taurates, acyl amino acids, acyl sarcosinates, sulfosuccinates, sulfonates, and mixtures thereof, wherein the alkyl and acyl groups of all these compounds comprise from 6 to 24 carbon atoms.

The anionic surfactant(s) that may be used may be alkyl sulfates, alkyl ether sulfates, alkylamido ether sulfates, alkylaryl polyether sulfates, monoglyceride sulfates, alkylsulfonates, alkylamide sulfonates, alkylarylsulfonates, alpha-olefin sulfonates, paraffin sulfonates, alkylsulfosuccinates, alkyl ether sulfosuccinates, alkylamide sulfosuccinates, alkyl sulfoacetates, acylsarcosinates, acylglutamates, alkylsulfosuccinamates, acylisethionates and N-acyltaurates, salts of alkyl monoesters and polyglycoside-polycarboxylic acids, acyllactylates, salts of D-galactoside uronic acids, salts of alkyl ether carboxylic acids, salts of alkyl aryl ether carboxylic acids, and salts of alkylamido ether carboxylic acids; or the non-salified forms of all of these compounds, the alkyl and acyl groups of all of these compounds containing from 6 to 24 carbon atoms and the aryl group denoting a phenyl group. Some of these compounds may be oxyethylenated and then preferably comprise from 1 to 50 ethylene oxide units. For example, the anionic surfactant may be chosen from sodium olefin sulfonates, e.g. sodium C14-C16 olefin sulfonate.

The salts of $C_6$-$C_{24}$ alkyl monoesters of polyglycoside-polycarboxylic acids may be chosen from $C_6$-$C_{24}$ alkyl polyglycoside-citrates, $C_6$-$C_{24}$ alkyl polyglycoside-tartrates, and $C_6$-$C_{24}$ alkyl polyglycoside-sulfo succinates.

When the anionic surfactant(s) are in salt form, they may be chosen especially from alkali metal salts such as the sodium or potassium salt and preferably the sodium salt, ammonium salts, amine salts and in particular amino alcohol salts, or alkaline-earth metal salts such as magnesium salts.

Examples of amino alcohol salts that may be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts. Alkali metal or alkaline-earth metal salts, such as sodium or magnesium salts, may be used.

Use is also made of $(C_6$-$C_{24})$alkyl sulfates, $(C_6$-$C_{24})$alkyl ether sulfates, which are optionally ethoxylated, comprising from 2 to 50 ethylene oxide units, and a mixture thereof, in particular in the form of alkali metal salts or alkaline-earth metal salts, ammonium salts or amino alcohol salts. In certain embodiments, the anionic surfactant(s) are chosen from $(C_{10}$-$C_{20})$alkyl ether sulfates, for example sodium lauryl ether sulfate.

Non-Ionic Surfactants

The hair color compositions may optionally comprise one or more non-ionic surfactants. Non-ionic surfactants are well known (see, e.g., in this regard, "Handbook of Surfactants" by M. R. Porter, Blackie & Son publishers (Glasgow and London), 1991, pp. 116-178, which is incorporated herein by reference in its entirety).

The non-ionic surfactant(s) can be, for example, selected from alcohols, alpha-diols, alkylphenols and esters of fatty acids, these compounds being ethoxylated, propoxylated or glycerolated and having at least one fatty chain comprising, for example, from 8 to 18 carbon atoms, it being possible for the number of ethylene oxide or propylene oxide groups to range from 2 to 50, and for the number of glycerol groups to range from 1 to 30. Maltose derivatives may also be mentioned. Non-limiting mention may also be made of copolymers of ethylene oxide and/or of propylene oxide; condensates of ethylene oxide and/or of propylene oxide with fatty alcohols; polyethoxylated fatty amides comprising, for example, from 2 to 30 mol of ethylene oxide; polyglycerolated fatty amides comprising, for example, from 1.5 to 5 glycerol groups, such as from 1.5 to 4; ethoxylated fatty acid esters of sorbitan comprising from 2 to 30 mol of ethylene oxide; ethoxylated oils from plant origin; fatty acid esters of sucrose; fatty acid esters of polyethylene glycol; polyethoxylated fatty acid mono or diesters of glycerol ($C_6$-$C_{24}$)alkylpolyglycosides; N—($C_6$-$C_{24}$)alkylglucamine derivatives, amine oxides such as ($C_{10}$-$C_{14}$)alkylamine oxides or N—($C_{10}$-$C_{14}$)acylaminopropylmorpholine oxides; and mixtures thereof.

The nonionic surfactants may optionally be chosen from polyoxyalkylenated or polyglycerolated nonionic surfactants. The oxyalkylene units are optionally oxyethylene or oxypropylene units, or a mixture thereof. Examples of oxyalkylenated nonionic surfactants that may be mentioned include: oxyalkylenated ($C_8$-$C_{24}$)alkylphenols, saturated or unsaturated, linear or branched, oxyalkylenated $C_8$-$C_{30}$ alcohols, saturated or unsaturated, linear or branched, oxyalkylenated $C_8$-$C_{30}$ amides, esters of saturated or unsaturated, linear or branched, $C_8$-$C_{30}$ acids and of polyethylene glycols, polyoxyalkylenated esters of saturated or unsaturated, linear or branched, $C_8$-$C_{30}$ acids and of sorbitol, saturated or unsaturated, oxyalkylenated plant oils, condensates of ethylene oxide and/or of propylene oxide, and mixtures thereof.

As examples of polyglycerolated nonionic surfactants, polyglycerolated $C_8$-$C_{40}$ alcohols are preferably used. In particular, the polyglycerolated $C_8$-$C_{40}$ alcohols correspond to the following formula (VII):

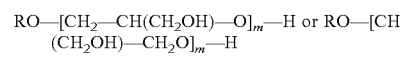

$$RO—[CH_2—CH(CH_2OH)—O]_m—H \text{ or } RO—[CH(CH_2OH)—CH_2O]_m—H$$

in which R represents a linear or branched $C_8$-$C_{40}$ and preferably $C_8$-$C_{30}$ alkyl or alkenyl radical, and m represents a number ranging from 1 to 30, and preferably from 1.5 to 10.

As examples of compounds that are suitable in the context of the invention, mention may be made of lauryl alcohol containing 4 mol of glycerol (INCI name: Polyglyceryl-4 Lauryl Ether), lauryl alcohol containing 1.5 mol of glycerol, oleyl alcohol containing 4 mol of glycerol (INCI name: Polyglyceryl-4 Oleyl Ether), oleyl alcohol containing 2 mol of glycerol (INCI name: Polyglyceryl-2 Oleyl Ether), cetearyl alcohol containing 2 mol of glycerol, cetearyl alcohol containing 6 mol of glycerol, oleocetyl alcohol containing 6 mol of glycerol, and octadecanol containing 6 mol of glycerol.

According to one embodiment, the nonionic surfactant may be selected from esters of polyols with fatty acids with a saturated or unsaturated chain containing for example from 8 to 24 carbon atoms, preferably 12 to 22 carbon atoms, and alkoxylated derivatives thereof, preferably with a number of alkyleneoxide of from 10 to 200, and more preferably from 10 to 100, such as glyceryl esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; polyethylene glycol esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; sorbitol esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; sugar (sucrose, glucose, alkylglycose) esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; ethers of fatty alcohols; ethers of sugar and a $C_8$-$C_{24}$, preferably $C_{12}$-$C_{22}$, fatty alcohol or alcohols; and mixtures thereof.

Preferably, the nonionic surfactant may be a nonionic surfactant with an HLB of 18.0 or less, such as from 4.0 to 18.0, more preferably from 6.0 to 15.0 and furthermore preferably from 9.0 to 13.0. The HLB is the ratio between the hydrophilic part and the lipophilic part in the molecule.

In some case, the nonionic surfactant is a fatty alkanolamide. Non-limiting examples of fatty alkanolamides that may be used include cocamide MEA, cocamide DEA, soyamide DEA, lauramide DEA, oleamide MIPA, stearamide MEA, myristamide DEA, stearamide DEA, oleylamide DEA, tallowamide DEA lauramide MIPA, tallowamide MEA, isostearamide DEA, isostearamide MEA, or mixtures thereof.

Amphoteric Surfactants

Hair color compositions according to the disclosure may optionally comprise one or more amphoteric surfactants. Non-limiting examples of amphoteric surfactants useful in the compositions include, for example, optionally quaternized secondary or tertiary aliphatic amine derivatives, in which the aliphatic group is a linear or branched chain comprising from 8 to 22 carbon atoms, said amine derivatives containing at least one anionic group, for instance a carboxylate, sulfonate, sulfate, phosphate or phosphonate group.

Mention may be made in particular of (C8-C20)alkylbetaines, sulfobetaines, (C8-C20)alkylsulfobetaines, (C8-C20)alkylamido(C1-C6)alkylbetaines, such as cocamidopropylbetaine, and (C8-C20)alkylamido(C1-C6) alkylsulfobetaines, and mixtures thereof. For example, mention may be made of compounds classified under the INCI names sodium cocoamphoacetate, sodium lauroamphoacetate, sodium caproamphoacetate, and sodium capryloamphoacetate.

Other compounds that may be chosen include disodium cocoamphodiacetate, disodium lauroamphodiacetate, disodium caproamphodiacetate, disodium capryloamphodiacetate, disodium cocoamphodipropionate, disodium lauroamphodipropionate, disodium caproamphodipropionate, disodium capryloamphodipropionate, lauroamphodipropionic acid, and cocoamphodipropionic acid.

Examples that may be mentioned include the cocoamphodiacetate sold by the company Rhodia under the trade name Miranol® $C_2M$ Concentrate, the sodium cocoamphoacetate sold under the trade name Miranol® Ultra C 32 and the product sold by the company Chimex under the trade name CHIMEXANE HA. In certain exemplary embodiments, the amphoteric surfactants are chosen from (C8-C20) alkylbetaines such as the one known under the INCI names coco-betaine, (C8-C20)alkylamido(C1-C6)alkylbetaines such as the one known under the INCI name cocamidopropylbetaine, and mixtures thereof. In one embodiment, the amphoteric surfactant is coco-betaine.

Thickening Agent

The hair color compositions optionally comprise one or more thickening agents. Thickening agents may be referred to as "gelling agents," "thickeners," or "viscosity modifying agents." Many thickening agents are water-soluble, and increase the viscosity of water or form an aqueous gel when dispersed/dissolved in water. The aqueous solution may be heated and cooled, or neutralized, for forming the gel, if necessary. The thickening agent may optionally be dispersed/dissolved in an aqueous solvent that is soluble in water, e.g., ethyl alcohol when it is dispersed/dissolved in water.

Non-limiting examples of thickening agents include xanthan gum, guar gum, biosaccharide gum, cellulose, acacia Seneca gum, sclerotium gum, agarose, pechtin, gellan gum, hyaluronic acid. In some instances, the one or more thickening agents may include polymeric thickening agents, for example, those selected from the group consisting of ammonium polyacryloyldimethyl taurate, ammonium acryloyldimethyltaurate NP copolymer, sodium polyacrylate, acrylates copolymers, polyacrylamide, carbomer, acrylates/C10-30 alkyl acrylate crosspolymer, and acrylamide/sodium acryloyldimethyltaurate copolymer.

In some instances, the thickening agent(s) are chosen from carboxylic acid polymers (e.g., carbomer), crosslinked polyacrylate polymers, polyacrylamide polymers, polysaccharides, gums, and mixtures thereof.

Further exemplary and non-limiting thickening agents include:

(a) Carboxylic Acid Polymers

These polymers are crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol.

Examples of commercially available carboxylic acid polymers useful herein include the carbomers, which are homopolymers of acrylic acid crosslinked with allyl ethers of sucrose or pentaerytritol. The carbomers are available as the Carbopol® 900 series from B.F. Goodrich (e.g., Carbopol) 954. In addition, other suitable carboxylic acid polymeric agents include Ultrez® 10 (B.F. Goodrich) and copolymers of C10-30 alkyl acrylates with one or more monomers of acrylic acid, methacrylic acid, or one of their short chain (e.g. C1-C4 alcohol) esters, wherein the crosslinking agent is an allyl ether of sucrose or pentaerytritol. These copolymers are known as acrylates/C10-C30 alkyl acrylate crosspolymers and are commercially available as Carbopol® 1342, Carbopol® 1382, Pemulen TR-1, and Pemulen TR-2, from B.F. Goodrich. In various exemplary embodiments, carboxylic acid polymer thickeners may be chosen from carbomers, acrylates/C10-C30 alkyl acrylate crosspolymers, and mixtures thereof.

(b) Crosslinked Polyacrylate Polymers

The compositions of the present disclosure may, in some embodiments, optionally contain crosslinked polyacrylate polymers useful as thickeners or gelling agents, such as, for example, cationic and nonionic polymers, and mixtures thereof.

(c) Polyacrylamide Polymers

The compositions of the present disclosure may optionally contain polyacrylamide polymers, for example polyacrylamide polymers including substituted branched or unbranched polymers. Among these polyacrylamide polymers is the polymer given the CTFA designation polyacrylamide and isoparaffin and laureth-7, available under the tradename Sepigel 305 from Seppic Corporation.

Other polyacrylamide polymers useful herein include multi-block copolymers of acrylamides and substituted acrylamides with acrylic acids and substituted acrylic acids. Commercially available examples of these multi-block copolymers include but are not limited to Hypan SR150H, SS500V, SS500W, and SSSA100H from Lipo Chemicals, Inc.

The compositions may also contain thickening and texturizing gels of the type exemplified by the product range called Lubrajel® from United Guardian.

(d) Polysaccharides

A wide variety of polysaccharides can be useful herein. As used herein, "polysaccharides" refer to gelling agents that contain a backbone of repeating sugar (i.e., carbohydrate) units. Nonlimiting examples of polysaccharide gelling agents include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Also useful herein are alkyl-substituted celluloses. Preferred among the alkyl hydroxyalkyl cellulose ethers is the material given the CTFA designation cetyl hydroxyethylcellulose, which is the ether of cetyl alcohol and hydroxyethylcellulose. This material is sold under the tradename Natrosol® CS Plus from Aqualon Corporation.

Other useful polysaccharides include scleroglucans comprising a linear chain of (1-3) linked glucose units with a (1-6) linked glucose every three units, a commercially available example of which is Clearogel™ CS11 from Michel Mercier Products Inc.

(e) Gums

Other thickening and gelling agents useful herein include materials which are primarily derived from natural sources. Nonlimiting examples of these gelling agent gums include acacia, agar, algin, alginic acid, ammonium alginate, amylopectin, calcium alginate, calcium carrageenan, camitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboxymethyl dextran, sodium carrageenan, tragacanth gum, xanthan gum, biosacharide gum, and mixtures thereof.

In various embodiments, water-soluble thickeners are chosen from water-soluble natural polymers, water-soluble synthetic polymers, clay minerals and silicic anhydride. Non-limiting examples of water-soluble natural polymers include gum arabic, tragacanth gum, karaya gum, guar gum, gellan gum, tara gum, locust bean gum, tamarind gum, sodium alginate, alginic acid propyleneglycol ester, carrageenan, farcelluran, agar, high-methoxy pectin, low-methoxy pectin, xanthine, chitosan, starch (for example starch derived from corn, potato, wheat, rice, sweet potato and tapioca, a-starch, soluble starch), fermentation polysaccharide (for example, xanthan gum, pullulan, carciran, dextran), acidic hetero-polysaccharide derived from callus of plants belonging to Polyantes sp. (for example, tuberous polysaccharide), proteins (for example, sodium casein, gelatin, albumin), chondroitin sulfate, and hyaluronic acid.

Non-limiting examples of water-soluble synthetic polymers include polyvinyl alcohol, sodium polyacrylate, sodium polymethacrylate, polyacrylic acid glycerin ester, carboxyvinyl polymer, polyacrylamide, polyvinyl pyrrolidone, polyvinyl methylether, polyvinyl sulfone, maleic acid copolymer, polyethylene oxide, polydiallyl amine, polyethylene imine, water soluble cellulose derivatives (for example, carboxymethyl cellulose, methyl cellulose, methylhydroxypropyl cellulose, hydroxyethyl cellulose, hydroxypropyl cellulose, cellulose sulfate sodium salt), and starch derivatives (for example, starch oxide, dialdehyde starch, dextrin, British gum, acetyl starch, starch phosphate, carboxymethyl starch, hydroxyethyl starch, hydroxypropyl starch).

Thickening agents may be nonionic, anionic, or cationic. In some instances, the thickening agents are preferably nonionic or anionic, more preferably, anionic.

Non-limiting examples of nonionic thickening agents include polysaccharides, modified or unmodified starches, amylose, amylopectin, glycogen, dextrans, celluloses, cellulose derivatives, xylans, glucans, arabans, galactans, chitin, agars, locust bean gums, mannans, and a mixture thereof. In some instances, the hair-coloring compositions preferably include nonionic thickening agent(s).

Non-limiting examples of anionic thickening agents include polyacrylate-3, carbomers, acrylates/C10-30 alkyl acrylate crosspolymers, acrylates/C10-30 alkyl acrylate crosspolymer, AMP-acrylates/allyl methacrylate copolymer, polyacrylate crosspolymer-6, a crosslinked methacrylic acid/ethyl acrylate copolymer (acrylates copolymer), and a mixture thereof. In some instances, the hair-coloring compositions preferably include anionic thickening agent(s), in particular, polyacrylate-3.

Non-limiting examples of cationic thickening agents include dimethylaminoethyl methacrylate homopolymers quaternized with methyl chloride or dimethylaminoethyl methacrylate copolymers quaternized with methyl chloride and acrylamide (e.g., methacryloylethyl trimethyl ammonium chloride homopolymer, INCI name: polyquaternium-37). Another suitable example of a cationic thickening agent is a product known by the INCI name of polyacrylate-1 crosspolymer. In some instances, the hair-coloring compositions may preferably exclude cationic thickening agents, i.e., the hair-coloring compositions may be free or essentially free of cationic thickening agents (or cationic thickening polymers).

The total amount of thickening agents in the hair-coloring compositions may vary but typically ranges from about 0.01% to about 10% by weight, based on the total weight of the hair-coloring composition. In some cases, the total amount of thickening agents range from about 0.01% to about 5%, about 0.01% to about 3%, about 0.1% to about 10%, about 0.1% to about 5%, or about 0.1% to about 3% by weight, based on the total weight of the hair-coloring compositions.

Hair Coloring Agent

The compositions according to the disclosure comprise at least one hair coloring agent. In various embodiments, the hair color compositions comprise at least two hair coloring agents.

In certain exemplary and non-limiting embodiments, the hair coloring agent(s) may be selected from direct dyes, including anionic, cationic and non-ionic direct dyes. For example, azo direct dyes, (poly)methine dyes such as cyanins, hemicyanins and styryls, carbonyl dyes, azine dyes, nitro(hetero)aryl dyes, tri(hetero)arylmethane dyes, porphyrin dyes, phthalocyanin dyes, and natural direct dyes, may be chosen. In certain embodiments, for example, the direct dyes may be chosen from nitrophenylenediamines, nitroaminophenols, azo dyes, anthraquinones, triarylmethane dyes, or indophenols, as well as salts thereof.

As suitable anionic (acid) direct dyes, for example, one or more compounds may be selected from the following group: Acid Yellow 1 (D&C Yellow 7, Citronin A, Ext. D&C Yellow No. 7, Japan Yellow 403, CI 10316, COLIPA no B001), Acid Yellow 3 (COLIPA no C 54, D&C Yellow No 10, Quinoline Yellow, E104, Food Yellow 13), Acid Yellow 9 (CI 13015), Acid Yellow 17 (CI 18965), Acid Yellow 23 (COLIPA no C 29, Covacap Jaune W 1100 (LCW), Sicovit Tartrazine 85 E 102 (BASF), Tartrazine, Food Yellow 4, Japan Yellow 4, FD&C Yellow No. 5), Acid Yellow 36 (CI 13065), Acid Yellow 121 (CI 18690), Acid Orange 6 (CI 14270), Acid Orange 7 (2-Naphthol orange, Orange II, CI 15510, D&C Orange 4, COLIPA no C015), Acid Orange 10 (CI 16230; Orange G sodium salt), Acid Orange 11 (CI 45370), Acid Orange 15 (CI 50120), Acid Orange 20 (CI 14600), Acid Orange 24 (BROWN 1; CI 20170; KATSU201; no sodium salt; Brown No. 201; RESORCIN BROWN; ACID ORANGE 24; Japan Brown 201; D & C Brown No. 1), Acid Red 14 (CI 14720), Acid Red 18 (E124, Red 18; CI 16255), Acid Red 27 (E 123, CI 16185, C-Rot 46, Echtrot D, FD&C Red No. 2, Food Red 9, Naphtholrot S), Acid Red 33 (Red 33, Fuchsia Red, D&C Red 33, CI 17200), Acid Red 35 (CI 18065), Acid Red 50, Acid Red 51 (CI 45430, Pyrosin B, Tetraiodofluorescein, Eosin J, Iodeosin), Acid Red 52 (CI 45100, Food Red 106, Solar Rhodamine B, Acid Rhodamine B, Red no 106 Pontacyl Brilliant Pink), Acid Red 73 (CI 27290), Acid Red 87 (Eosin, CI 45380), Acid Red 88, Acid Red 92 (D&C Red 104; AKA231; RED 28; SUREDYE; 11969 Red; PHLOXINE; CI 45405; CI 45410; EOSINE B); Acid Red 95 (CI 45425, Erythrosine, Simacid Erythrosine Y), Acid Red 155, Acid Red 180, Acid Red 184 (CI 15685), Acid Red 195; Pigment Red 57:1 (E180; D & C RED 7; CI 15850; Rubine 4BN; CI 15850:1; PIGMENT RED 57; Litholrubine BK; Litholrubine RB; Litholrubine BCA; Litholrubine B); Acid Violet 9, Acid Violet 43 (Jarocol Violet 43, Ext. D&C Violet No. 2, CI 60730, COLIPA no C063), Acid Violet 49 (CI 42640), Acid Violet 50 (CI 50325), Acid Blue 1 (Patent Blue, CI 42045), Acid Blue 3 (Patent Blue V, CI 42051), Acid Blue 7 (CI 42080), Acid Blue 104 (CI 42735), Acid Blue 9 (E 133, Patent Blue AE, Amido Blue AE, Erioglaucine A, CI 42090, CI Food Blue 2), Acid Blue 62 (CI 62045), Acid Blue 74 (E 132, CI 73015), Acid Blue 80 (CI 61585), Acid Green 3 (CI 42085, Food Green1), Acid Green 5 (CI 42095), Acid Green 9 (CI 42100), Acid Green 22 (CI 42170), Acid Green 25 (CI 61570, Japan Green 201, D&C Green No. 5), Acid Green 50 (Brilliant Acid Green BS, CI 44090, Acid Brilliant Green BS, E 142), Acid Black 1 (Black No 401, Naphthalene Black 10B, Amido Black 10B, CI 20470, COLIPA no B15), Acid Black 52 (CI 15711), Food Yellow 8 (CI 14270), Food Blue 5, D&C Yellow 8, D&C Green 5, D&C Orange 10, D&C Orange 11, D&C Red 21, D&C Red 27, D&C Red 33, D&C Brown 1, bromophenol blue, tetrabromophenol blue, and mixtures thereof.

In a further embodiment, the hair coloring agent may be selected from the group including Acid Yellow 1, Acid Yellow 3, Acid Yellow 9, Acid Yellow 17, Acid Yellow 23, Acid Yellow 36, Acid Yellow 121, Acid Orange 6, Acid Orange 7, Acid Orange 10, Acid Orange 11, Acid Orange 15, Acid Orange 20, Acid Orange 24, Acid Red 14, Acid Red 18, Acid Red 27, Acid Red 33, Acid Red 35, Acid Red 51, Acid Red 52, Acid Red 73, Acid Red 87, Acid Red 92, Acid Red 95, Acid Red 184, Acid Red 195, Acid Violet 43, Acid Violet 49, Acid Violet 50, Acid Blue 1, Acid Blue 3, Acid Blue 7, Acid Blue 104, Acid Blue 9, Acid Blue 62, Acid Blue 74, Acid Blue 80, Acid Green 3, Acid Green 5, Acid Green 9, Acid Green 22, Acid Green 25, Acid Green 50, Acid Black 1, Acid Black 52, Food Yellow 8, Food Blue 5, D&C Yellow 7, D&C Yellow 8, D&C Orange 4, D&C Green 5, D&C Green 8, D&C Orange 10, D&C Orange 11, D&C Red 21, D&C Red 27, D&C Red 33, D&C Violet 2, D&C Brown 1, and mixtures thereof.

Non-limiting examples of suitable cationic (basic) dyes include those in the following group: Basic Blue 6 (CI-No. 51,175), Basic Blue 7 (CI-No. 42,595) Basic Blue 9 (CI-No. 52,015), Basic Blue 26 (CI-No. 44,045), Basic Blue 41 (CI-No. 11,154), Basic Blue 99 (CI-No. 56,059), HC Blue 15, HC Blue 16 (Blue Quat Bromide), Cationic Blue 347, Basic Brown 4 (CI-No. 21,010), Basic Brown 16 (CI-No. 12,250), Basic Brown 17 (CI-No. 12,251), Natural Brown 7 (CI-No. 75,500), Basic Green 1 (CI-No. 42,040), Basic Red 2 (CI-No. 50,240), Basic Red 12, Basic Red 22 (CI-No. 11,055), Basic Red 51, Basic Red 76 (CI-No. 12,245), Basic Violet 1 (CI-No. 42,535), Basic Violet 2, Basic Violet 3 (CI-No. 42,555), Basic Violet 10 (CI-No. 45,170), Basic Violet 14 (CI-No. 42,510), Basic Yellow 57 (CI-No. 12,719), Basic Yellow 87, Basic Orange 31, and mixtures thereof.

Additional useful cationic direct dyes include hydrazono cationic dyes of formulas (IXa) and (IX'a), the azo cationic dyes (Xa) and (X'a) and the diazo cationic dyes (XIa) below:

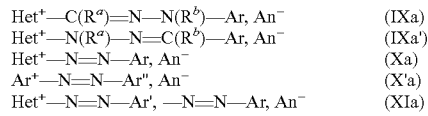

| | |
|---|---|
| Het⁺—C(Rᵃ)=N—N(Rᵇ)—Ar, An⁻ | (IXa) |
| Het⁺—N(Rᵃ)—N=C(Rᵇ)—Ar, An⁻ | (IXa') |
| Het⁺—N=N—Ar, An⁻ | (Xa) |
| Ar⁺—N=N—Ar'', An⁻ | (X'a) |
| Het⁺—N=N—Ar', —N=N—Ar, An⁻ | (XIa) | in which formulas (IXa), (IX'a), (Xa), (X'a) and (XIa):

Het⁺ represents a cationic heteroaryl radical, preferably bearing an endocyclic cationic charge, such as imidazolium, indolium or pyridinium, optionally substituted preferentially with one or more ($C_1$-$C_8$) alkyl groups such as methyl;

Ar⁺ representing an aryl radical, such as phenyl or naphthyl, bearing an exocyclic cationic charge, preferentially ammonium, particularly tri($C_1$-$C_8$)alkylammonium such as trimethylammonium;

Ar represents an aryl group, especially phenyl, which is optionally substituted, preferentially with one or more electron-donating groups such as i) optionally substituted ($C_1$-$C_8$)alkyl, ii) optionally substituted ($C_1$-$C_8$) alkoxy, iii) (di)($C_1$-$C_8$)(alkyl)amino optionally substituted on the alkyl group(s) with a hydroxyl group, iv) aryl($C_1$-$C_8$)alkylamino, v) optionally substituted N—($C_1$-$C_8$)alkyl-N-aryl($C_1$-$C_8$)alkylamino, or alternatively Ar represents a julolidine group;

Ar' is an optionally substituted divalent (hetero)arylene group such as phenylene, particularly para-phenylene, or naphthalene, which are optionally substituted, preferentially with one or more groups ($C_1$-$C_8$)alkyl, hydroxyl or ($C_1$-$C_8$)alkoxy;

Ar" is an optionally substituted (hetero)aryl group such as phenyl or pyrazolyl, which are optionally substituted, preferentially with one or more groups $(C_1-C_8)$alkyl, hydroxyl, (di)$(C_1-C_8)$(alkyl)amino, $(C_1-C_8)$alkoxy or phenyl;

$R^a$ and $R^b$, which may be identical or different, represent a hydrogen atom or a group $(C_1-C_8)$alkyl, which is optionally substituted, preferentially with a hydroxyl group;

or alternatively the substituent $R^a$ with a substituent of Het$^+$ and/or $R_b$ with a substituent of Ar and/or $R^a$ with $R_b$ form, together with the atoms that bear them, a (hetero)cycloalkyl;

particularly, $R^a$ and $R_b$ represent a hydrogen atom or a group $(C_1-C_4)$alkyl, which is optionally substituted with a hydroxyl group; and An$^-$ represents an anionic counter-ion such as mesylate or halide.

In particular, mention may be made of the azo and hydrazono cationic dyes bearing an endocyclic cationic charge of formulae (IXa), (IX'a) and (Xa). More particularly those of formulae (IXa), (IX'a) and (Xa) derived from the dyes described in patent applications WO 95/15144, WO 95/01772, and EP-714954, which are incorporated herein by reference in their entirety.

In some cases, the cationic part is derived from the following derivatives:

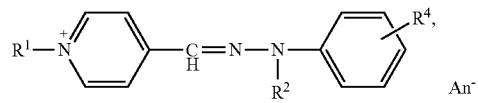

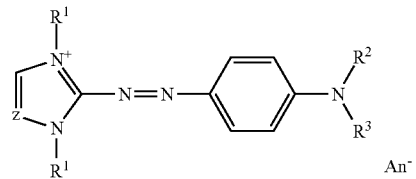

wherein:
$R^1$ representing a $(C_1-C_4)$ alkyl group such as methyl;

$R^2$ and $R^3$, which are identical or different, represent a hydrogen atom or a $(C_1-C_4)$alkyl group, such as methyl;

$R^4$ represents a hydrogen atom or an electron-donating group such as optionally substituted $(C_1-C_8)$alkyl, optionally substituted $(C_1-C_8)$alkoxy, or (di)$(C_1-C_8)$(alkyl)amino optionally substituted on the alkyl group(s) with a hydroxyl group; particularly, $R^4$ is a hydrogen atom;

Z represents a CH group or a nitrogen atom, preferentially CH; and

An$^-$ represents an anionic counter-ion such as mesylate or halide.

For example, the direct dye may be chosen from Basic Red 51, Basic Yellow 87 and Basic Orange 31, derivatives thereof, or mixtures thereof:

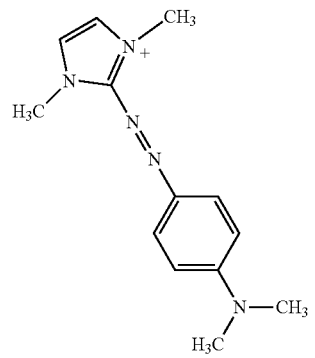
Basic Red 51

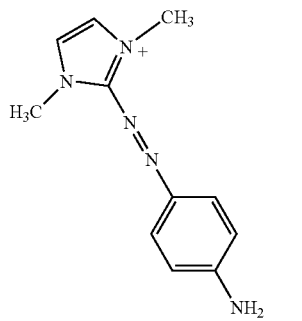
Basic Orange 31

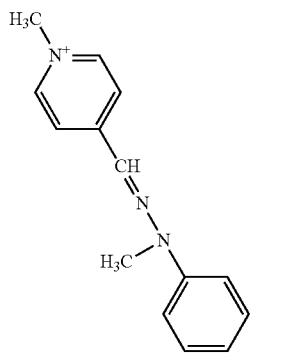
Basic Yellow 87

In yet further exemplary embodiments, at least one non-ionic direct dye may be chosen from the following group: HC Yellow 2, HC Yellow 4, HC Yellow 5, HC Yellow 6, HC Yellow No. 7, HC Yellow No. 8, HC Yellow No. 9, HC Yellow No. 10, HC Yellow No. 11, HC Yellow 12, HC Yellow No. 13, HC Yellow No. 14, HC Yellow No. 15, HC Green No. 1, HC Orange 1, HC Orange No. 2, HC Orange No. 3, HC Orange No. 5, Disperse Orange 3, HC Red 1, HC Red 3, HC Red 7, HC Red No. 8, HC Red No. 9, HC Red 10, HC Red 11, HC Red 13, HC Red No. 54, HC Red No. 14, HC Red BN, HC Blue 2, HC Blue No. 4, HC Blue No. 5, HC Blue No. 6, HC Blue No. 7, HC Blue No. 8, HC Blue No. 9, HC Blue No. 10, HC Blue 11, HC Blue 12, HC Blue No. 13, HC Blue 15, HC Blue No. 17, Disperse Blue 3, HC Violet BS, HC Violet 1, HC Violet No. 2, Disperse Violet 1, Disperse Violet 4, Disperse Black 9, HC Brown No. 1, HC Brown No. 2, 1,4-diamino-2-nitrobenzene, 1,2-diamino-4-nitrobenzol, 2-amino-4-nitrophenol, 1,4-bis(2-hydroxyethyl)-amino-2-nitrobenzene, 3-nitro-4-(2-hydroxyethyl)aminophenol, 2-(2-hydroxyethyl) amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 1-hydroxy-2-amino-3-nitrobenzol, 4-amino-3-nitrophenol, 1-(2'-ureidoethyl)amino-4-nitrobenzene, 2-[(4-amino-2-nitrophenyl)amino]benzoic acid, 4-[(3-hydroxypropyl)amino]-3-nitrophenol, 4-nitro-o-phenylenediamine, 6-nitro-1,2,3,4-tetrahydroquinoxaline, 2-hydroxy-1,4-naphthoquinone, picramic acid and its salts, N,N'-bis(2-hydroxyethyl)-2-nitro-p-phenylenediamine, 2-amino-6-chloro-4-nitropheneol, 4-ethylamino-3-nitrobenzoic acid, 2-chloro-6-ethylamino-4-nitrophenol, and mixtures thereof.

Without being limiting, particularly useful direct dyes include Basic Yellow 87, HC Violet No. 2, Basic Orange 31, HC Blue No. 15, Basic Violet 2, and mixtures thereof.

In further exemplary and non-limiting embodiments, the hair coloring agent(s) may be selected from pigments. The term "pigment" is understood to refer to a white or colored solid particle, which is naturally insoluble in the liquid hydrophilic and lipophilic phases usually used in cosmetics, or which is made insoluble by formulation in the form of a lake, where appropriate.

By way of non-limiting example, azo pigments containing one or more azo groups may be chosen:

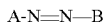

where:
A is chosen from an optionally substituted (hetero)aryl,
B is chosen from optionally substituted (hetero)aryl or —CH[C(O)—R]—C(O)—X1-A';
  where A' represents an optionally substituted (hetero)aryl and R represents a hydrogen atom or a group (C1-C6)alkyl,
wherein the groups A, A', and B may optionally be (hetero)aryls that do not contain any solubilizing groups such as —SO₃H or —COOH.

Exemplary useful pigments may, for example, include monoazo pigments such as ß-naphthols, monoazopyrrolones, benzimidazolone pigments; diazo pigments such as diazodiarylide pigments and bis(N-acetoacetarylide); triazo; and tetraazo pigments. Mention may also be made of azo metal complex pigments.

In yet further exemplary embodiments, other pigments such as isoindolinone and isoindoline pigments, phthalocyanin pigments; quinacridone pigments; perinone pigments; perylene pigments; anthraquinone pigments such as hydroxyanthraquinone pigments; aminoanthraquinone pigments including acylaminoanthraquinones and azo anthraquinone pigments; heterocyclic anthraquinones; polycarboxylic anthraquinone pigments, pyranthrone pigments; anthranthrone pigments; diketopyrrolopyrrole (DPP) pigments; thioindigo pigments; dioxazine pigments; triphenylmethane pigments; quinophthalone pigments; and fluorescent pigments may be chosen.

In certain embodiments, the pigment may be at least partly organic. According to one embodiment, the pigment is an organic pigment.

As non-limiting examples of pigments, carbon black, titanium oxide, chromium oxide, pigments of D&C or FD&C type and lakes thereof, and especially those known under the names D&C Blue No. 4, D&C Brown No. 1, FD&C Green No. 3, D&C Green No. 5, D&C Green No. 6, FD&C Green No. 8, D&C Orange No. 4, D&C Orange No. 5, D&C Orange No. 10, D&C Orange No. 11, FD&C Red No. 4, D&C Red No. 6, D&C Red No. 7, D&C Red No. 17, D&C Red No. 21, D&C Red No. 22, D&C Red No. 27, D&C Red No. 28, D&C Red No. 30, D&C Red No. 31, D&C Red No. 33, D&C Red No. 34, D&C Red No. 36, FD&C Red No. 40, FD&C Red 40 lake, D&C Violet No. 2, FD & C Blue No. 1, D&C Yellow No. 6, FD&C Yellow No. 6, D&C Yellow No. 7, Ext. D&C Yellow No. 7, D&C Yellow No. 8, D&C Yellow No. 10, and D&C Yellow No. 11 may be chosen.

As further non-limiting examples, mention may be made of mineral pigments. Mineral pigments may or may not be surface-treated and/or coated. For example, titanium dioxide, zirconium oxide, or cerium oxide, and also zinc oxide, iron oxide (black, yellow, or red) or chromium oxide, manganese violet, ultramarine blue, chromium hydrate and ferric blue, or alternatively metal powders, for instance aluminium powder, copper powder, gold powder, and silver powder may be chosen.

It should be understood that more than one hair coloring agent may be chosen. Thus, hair coloring compositions according to the disclosure may comprise mixtures or combinations of hair coloring agents, such as, by way of non-limiting example, at least two direct dyes, at least two pigments, or at least one direct dye and at least one pigment, at least one direct dye and at least two pigments, at least two direct dyes and at least one pigment, etc.

In various embodiments, the hair coloring agent(s) are limited to direct dyes. In further embodiments, the hair coloring agent(s) are limited to combinations of direct dyes and pigments. In yet further embodiments, the hair coloring compositions do not include any oxidative dyes, i.e. oxidation dye precursors.

In various embodiments, the one or more hair coloring agents may be present in an amount ranging from about 0.001% to about 10% by weight, such as from about 0.01% to about 10%, about 0.1% to about 10%, about 0.01% to about 5%, about 0.1% to about 5%, about 0.01% to about 5%, about 0.1% to about 5%, about 0.01% to about 4%, about 0.1% to about 4%, about 0.01% to about 3%, about 0.1% to about 3%, about 0.01% to about 2.5%, about 0.1% to about 2.5%, about 0.01% to about 2%, about 0.1% to about 2%, about 0.01% to about 1.5%, about 0.1% to about 1.5%, about 0.01% to about 1%, or about 0.1% to about 1% by weight, of the total weight of the composition.

Cationic Polymer

The hair coloring compositions may optionally comprise at least one cationic polymer. The cationic polymer may be chosen from cationic associative polymers comprising, in their structure, a pendent or terminal hydrophobic chain, for example of alkyl or alkenyl type, containing from 10 to 30 carbon atoms.

The at least one cationic polymer can be chosen from, for example: (1) Homopolymers and copolymers derived from acrylic or methacrylic esters or amides, examples of which include copolymers of acrylamide and of dimethylaminoethyl acrylate quaternized with dimethyl sulfate or with a dimethyl halide, such as the product sold under the name HERCOFLOC by the company Hercules, copolymers of acrylamide and of methacryloyloxyethyltrimethylammonium chloride described, for example, in EP 80 976 and sold under the name BINA QUAT P 100 by the company Ciba Geigy, the copolymer of acrylamide and of methacryloyloxyethyltrimethylammonium methosulfate sold under the name RETEN by the company Hercules, quaternized or non-quaternized vinylpyrrolidone/dialkylaminoalkyl acrylate or acrylate copolymers, such as the products sold under the name GAFQUAT by the company ISP, for instance GAFQUAT 734 or GAFQUAT 755, or alternatively the products known as COPOLYMER 845, 958 and 937, dimethylaminoethyl acrylate/vinylcaprolactam/vinylpyrrolidone terpolymers, such as the product sold under the name GAFFIX VC 713 by the company ISP, vinylpyrrolidone/methacrylamidopropyldimethylamine copolymers sold, for example, under the name STYLEZE CC 10 by ISP, quaternized vinylpyrrolidone/dimethylaminopropylmethacrylamide copolymers such as the product sold under the name GAFQUAT HS 100 by the company ISP, and crosslinked polymers of methacryloyloxy(C1-C4)alkyltri(C1-C4)alkylammonium salts such as the polymers obtained by homopolymerization of dimethylaminoethyl acrylate quaternized with methyl chloride, or by copolymerization of acrylamide with dimethylaminoethyl acrylate quaternized with methyl chloride, the homo- or copolymerization being followed by crosslinking with a compound containing olefinic unsaturation, such as methylenebisacrylamide.

In some embodiments, a crosslinked acrylamide/methacryloyloxyethyltri-methylammonium chloride copolymer (20/80 by weight) in the form of a dispersion containing 50% by weight of the copolymer in mineral oil can be used. This dispersion is sold under the name SALCARE® SC 92 by the company Ciba. In some embodiments, a crosslinked methacryloyloxyethyltrimethylammonium chloride homopolymer containing about 50% by weight of the homopolymer in mineral oil or in a liquid ester can be used. These dispersions are sold under the names SALCARE® SC 95 and SALCARE® SC 96 by the company Ciba.

Other examples are cellulose ether derivatives comprising quaternary ammonium groups, such as the polymers sold under the names JR (JR 400, JR 125, JR 30M) or LR (LR 400, LR 30M) by the company Union Carbide Corporation. (2) Celluloses such as hydroxymethyl-, hydroxyethyl- or hydroxy-propylcelluloses, or copolymers of cellulose or cellulose derivatives grafted with a water-soluble quaternary ammonium monomer, such as hydroxymethyl-, hydroxyethyl- or hydroxy-propylcelluloses grafted, for instance, with a methacryloylethyltrimethylammonium, methacrylamidopropyltrimethylammonium or dimethyldiallylammonium salt. These are sold under the name CELQUAT L 200 and CELQUAT H 100 by the company National Starch.

Further examples include: (3) Non-cellulose cationic polysaccharides, such as guar gums containing trialkylammonium cationic groups. Such products are sold, for example, under the trade names JAGUAR C135, JAGUAR C15, JAGUAR C17 and JAGUAR C162 by the company Meyhall; (4) Polymers of piperazinyl units and of divalent alkylene or hydroxyalkylene radicals; (5) Water-soluble polyamino amides prepared, for example, by polycondensation of an acidic compound with a polyamine; these polyamino amides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or alternatively with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative; the crosslinking agent being used in an amount ranging from 0.025 to 0.35 mol per amine group of the polyamino amide; these polyamino amides can be alkylated or, if they contain at least one tertiary amine function, they can be quaternized. Exemplary mention may be made of the adipic acid/dimethylaminohydroxypropyl/diethylenetriamine polymers sold under the name CARTARETINE F, F4 or F8 by the company Sandoz; (6) Polymers obtained by reaction of at least one polyalkylene polyamine containing two primary amine groups and at least one secondary amine group with a dicarboxylic acid chosen from diglycolic acid and saturated C3-C8 aliphatic dicarboxylic acids. The molar ratio between the polyalkylene polyamine and the dicarboxylic acid ranges from 0.8:1 to 1.4:1; the polyamino amide resulting therefrom is reacted with epichlorohydrin in a molar ratio of epichlorohydrin relative to the secondary amine group of the polyamino amide ranging from 0.5:1 to 1.8:1. Polymers of this type are sold, for example, under the name HERCOSETT 57, PD 170 or DELSETTE 101 by the company Hercules; (7) Cyclopolymers of alkyldiallylamine and of dialkyldiallylammonium, such as for example: dimethyldiallylammonium chloride homopolymer sold under the name MERQUAT® 100 and MERQUAT® 280 by the company Nalco (and its homologues of low weight-average molecular mass) and the copolymers of diallyldimethylammonium chloride and of acrylamide, sold under the name MERQUAT® 550; (8) Quaternary diammonium polymers; (9) Polyquaternary ammonium polymers; examples that may be mentioned include the products MIRAPOL A 15, MIRAPOL AD1, MIRAPOL AZ1 and MIRAPOL 175 sold by the company Miranol; (10) Quaternary polymers of vinylpyrrolidone and of vinylimidazole, for instance the products sold under the names LUVIQUAT FC 905, FC 550 and FC 370 by the company BASF; (11) Vinylamide homopolymers or copolymers, such as partially hydrolysed vinylamide homopolymers such as poly(vinylamine/vinylamide)s; (12) Cationic polyurethane derivatives, for example those of elastic nature formed from the reaction:
- (a1) of at least one cationic unit resulting from at least one tertiary or quaternary amine bearing at least two reactive functions containing labile hydrogen,
- (a2) of at least one mixture of at least two different nonionic units bearing at least two reactive functions containing labile hydrogen, for instance chosen from hydroxyl groups, primary or secondary amine groups, and thiol groups, and
- (b) of at least one compound comprising at least two isocyanate functions.

Other cationic polymers that may be used in the context of the disclosure include, for example, (13) cationic proteins or cationic protein hydrolysates, polyalkyleneimines, such as polyethyleneimines, polymers containing vinylpyridine or vinylpyridinium units, and chitin derivatives.

By way of non-limiting example, useful cationic polymers include polyquaternium 4, polyquaternium 6, polyquaternium 7, polyquaternium 10, polyquaternium 11, polyquaternium 16, polyquaternium 22, polyquaternium 28, polyquaternium 32, polyquaternium-46, polyquaternium-51, polyquaternium-52, polyquaternium-53, polyquaternium-54, polyquaternium-55, polyquaternium-56, polyquaternium-57, polyquaternium-58, polyquaternium-59, polyquaternium-60, polyquaternium-63, polyquaternium-64, polyquaternium-65, polyquaternium-66, polyquaternium-67, polyquaternium-70, polyquaternium-73, polyquaternium-74, polyquaternium-75, polyquaternium-76, polyquaternium-77, polyquaternium-78, polyquaternium-79, polyquaternium-80, polyquaternium-81, polyquaternium-82, polyquaternium-84, polyquaternium-85, polyquaternium-86, polyquaternium-87, polyquaternium-90, polyquaternium-91, polyquaternium-92, polyquaternium-94, and guar hydroxypropyltrimonium chloride, as well as mixtures thereof.

Exemplary useful cationic polymers include hydroxyethylcellulose, guar hydroxypropyltrimonium chloride, and combinations thereof.

The at least one cationic polymer may be present in an amount up to about 5%, such as, for example, an amount ranging from about 0.001% to about 5%, about 0.01% to about 5%, about 0.1% to about 5% by weight, based on the total weight of the composition. For example, the at least one cationic polymer may be present in an amount ranging from about 0.001% to about 2%, about 0.01% to about 2%, about 0.1% to about 2%, from about 0.001% to about 1%, about 0.01% to about 1%, or about 0.1% to about 1% by weight, based on the total weight of the composition.

Solvent

The hair color compositions according to the disclosure comprise a solvent. The solvent may be chosen from water, non-aqueous solvents, or mixtures thereof.

The solvent may be present in the hair color composition in an amount ranging from about 10% to about 98% by weight, relative to the total weight of the hair color composition. For example, the total amount of solvent may range from about 80% to about 98%, about 80% to about 95%, about 80% to 93%, or about 80% to about 90% by weight, relative to the total weight of the hair color composition.

In some embodiments, the solvent comprises, consists essentially of, or consists of water. The total amount of water in the hair color compositions may vary depending on the type of composition and the desired consistency, viscosity, etc. In some embodiments, the total amount of water is about 10% to about 98% by weight, relative to the total weight of the hair color composition, including all ranges and subranges therebetween. For example, in one embodiment, the total amount of water may be about 80% to about 98%, about 80% to about 95%, about 80% to 93%, or about 80% to 90% by weight, relative to the total weight of the hair color composition. In further embodiments, the water may be present in an amount ranging from about 60% to about 95%, about 60% to about 90%, about 60% to about 85%, about 60% to about 80%, about 65% to about 95%, about 65% to about 90%, about 65% to about 85%, about 65% to about 80%, about 70% to about 95%, about 70% to about 90%, about 70% to about 85%, about 70% to about 80%, about 75% to about 95%, about 75% to about 90%, or about 75% to about 85% by weight, relative to the total weight of the hair color composition.

In certain embodiments, the composition comprises, consists essentially of, or consists of non-aqueous solvents, for example, glycerin, $C_{1-4}$ alcohols, organic solvents, fatty alcohols, fatty ethers, fatty esters, polyols, glycols, vegetable oils, mineral oils, liposomes, laminar lipid materials, and mixtures thereof. As examples of organic solvents, non-limiting mentions can be made of monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerin. The organic solvents can be volatile or non-volatile compounds.

Further non-limiting examples of solvents which may be used include alkanediols (polyhydric alcohols) such as glycerin, 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, caprylyl glycol, 1,2-hexanediol, 1,2-pentanediol, and 4-methyl-1,2-pentanediol; alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbit, sorbitan, acetine, diacetine, triacetine, sulfolane, and mixtures thereof.

In some cases, the water-soluble solvent may be selected from the group consisting of one or more glycols, $C_{1-4}$ alcohols, glycerin, and a mixture thereof. In some cases, the water-soluble solvent is selected from the group consisting of hexylene glycol, proplene glycol, caprylyl glycol, glycerin, isopropyl alcohol, and mixtures thereof.

Polyhydric alcohols are useful. Examples of polyhydric alcohols include glycerin, ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, 1,2,6-hexanetriol, and mixtures thereof.

Polyol compounds may also be used. Non-limiting examples include the aliphatic diols, such as 2-ethyl-2-methyl-1,3-propanediol, 3,3-dimethyl-1,2-butanediol, 2,2-diethyl-1,3-propanediol, 2-methyl-2-propyl-1,3-propanediol, 2,4-dimethyl-2,4-pentanediol, 2,5-dimethyl-2,5-hexanediol, 5-hexene-1,2-diol, and 2-ethyl-1,3-hexanediol, and mixtures thereof.

The total amount of the non-aqueous solvents may vary, but in some cases ranges from about 0.01% to about 50% by weight, relative to the total weight of the composition. For example, the total amount of non-aqueous solvents may range from about 1% to about 50%, about 2% to about 50%, about 3% to 50%, about 4% to about 50%, about 5% to about 50%, 1% to about 40%, about 2% to about 40%, about 3% to 40%, about 4% to about 40%, about 5% to about 40%, about 1% to about 35%, about 2% to about 35%, about 3% to 35%, about 4% to about 35%, or about 5% to about 35% by weight, relative to the total weight of the composition. In further embodiments, the total amount of non-aqueous solvents may range from about 1% to about 10%, about 2% to about 8%, about 3% to about 7%, about 25% to about 45%, about 25% to about 40%, about 25% to about 35%, or about 30% to about 35% by weight, relative to the total weight of the composition.

In various embodiments, the solvent comprises a combination of water and non-aqueous solvents. In one embodiment, the solvent comprises a combination of water, at least one glycol, and at least one alcohol.

pH Adjusters

The hair color compositions according to the disclosure have a pH (+/−0.3) ranging up to about 7.5, such as from about 2 to about 7.5, about 2 to about 7, about 2 to about 6, about 2 to about 6.5 about 2 to about 5.5, about 2 to about 5, about 2 to about 4.5, about 2 to about 4, about 2 to about 3.5, about 2 to about 3, about 2.5 to about 6, about 2.5 to about 5.5, about 2.5 to about 5, about 2.5 to about 4.5, about 2.5 to about 4, about 2.5 to about 3.5, about 2.5 to about 3, about 3 to about 6, about 3 to about 5.5, about 3 to about 5, about 3 to about 4.5, about 3 to about 4, about 3 to about 3.5, about 3.5 to about 6, about 3.5 to about 5.5, about 3.5 to about 5, about 3.5 to about 4.5, or about 3.5 to about 4. For example, the hair color compositions may have a pH (+/−0.3) of about 2.0, about 2.1, about 2.2., about 2.3, about 2.4, about 2.5, about 2.6, about 2.7, about 2.8, about 2.9, about 2.0, about 3.1, about 3.2, about 3.3, about 3.4, about 3.5, about 3.6, about 3.7, about 3.8, about 3.9, 4.0, about 4.1, about 4.2, about 4.3, about 4.4, about 4.5, about 4.6, about 4.7, about 4.8, about 4.9, about 5, about 5.5, about 6, about 6.5, about 7, or about 7.5. In certain embodiments, the pH (+/−0.3) of the hair coloring compositions is less than 7, for example ranges from about 2 up to less than 7, or from about 2.5 up to less than 7, about 3 up to less than 7, about 3.5 up to less than 7, about 4 up to less than 7, about 4.5 up to less than 7, about 5 up to less than 7, about 5.5 up to less than 7, about 6 up to less than 7, or about 6.5 up to less than 7. In yet further embodiments, the hair coloring compositions may have a pH (+/−0.3) ranging from about 3 to about 6.7, about 2.5 to about 6.5, about 3.5 to about 6, about 3.5 to about 5.5, about 3.5 to about 5, or about 3.5 to about 4.5. The composition may therefore, optionally contain pH adjusters, which are well known in the cosmetic treatment of keratin fibers, such as hair.

Additional Components

The compositions according to the disclosure may optionally comprise any auxiliary or additional component suitable for use in cosmetic compositions, and in particular suitable for hair color compositions. Such components may include, but are not limited to, dyes/pigments in addition to those listed above, ceramides, film forming agents or polymers, humectants and moisturizing agents, fatty substances other than fatty alcohols, emulsifying agents, fillers, structuring agents, propellants, shine agents, antioxidants or reducing agents, penetrants, sequestrants, fragrances, buffers, dispersants, plant extracts, volatile or non-volatile, modified or unmodified silicones, preserving agents, opacifiers, sunscreen agents, vitamins, and antistatic agents.

Methods

It has been discovered that compositions according to the disclosure surprisingly impart improved properties to the hair, such as strength, shine, conditioning, feel, detangling, and/or combability, while also imparting excellent evenness of color to the hair, during processes for altering the color of the hair. Therefore, another aspect of the invention pertains to methods of using any of the compositions described herein by applying the compositions to the hair, for example methods of altering the color of the hair and/or methods of imparting any of the beneficial properties described herein to the hair, e.g. strengthening or caring.

In one embodiment, the method comprises applying the hair color compositions directly to hair. Optionally, the hair color compositions may be applied to the hair following a process for bleaching the hair.

The hair color composition or the mixture may be left on the hair for a period of time sufficient to achieve the desired effect. For example, the hair composition or the mixture may be left on the hair for up to one hour, such as from about 3 minutes to about 45 minutes, from about 5 minutes to about 40 minutes, from about 10 minutes to about 35 minutes, or from about 15 minutes to about 30 minutes. One skilled in the art will be able to determine an appropriate amount of time to leave the hair color composition or the mixture on the hair in order to achieve the desired effect.

Although not required, the hair may be heated, such as with a hair dryer or hood, while the hair color composition is on the hair. The composition may, optionally, be rinsed from the hair, and may optionally be followed by washing the hair in any conventional manner.

As used herein, the terms "comprising," "having," and "including" (or "comprise," "have," and "include") are used in their open, non-limiting sense.

The terms "a," "an," and "the" are understood to encompass the plural as well as the singular.

Thus, the term "a mixture thereof" or "a combination thereof" also relates to "mixtures thereof" and "combinations thereof." Throughout the disclosure, the terms "a mixture thereof" and "a combination thereof" is used, following a list of elements as shown in the following example where letters A-F represent the elements: "one or more elements selected from the group consisting of A, B, C, D, E, F, and a mixture thereof." The terms "a mixture thereof" or "a combination thereof" do not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, and a mixture thereof," it indicates that that one or more of A, B, C, D, and F may be included, one or more of a salt of A, a salt of B, a salt of C, a salt of D, a salt of E, and a salt of F may be include, or a mixture of any two of A, B, C, D, E, F, a salt of A, a salt of B, a salt of C, a salt of D, a salt of E, and a salt of F may be included.

The salts, for example, the salts of the amino acids, the amino sulfonic acids, and the non-polymeric mono, di, and/or tricarboxylic acids, which are referred to throughout the disclosure may include salts having a counter-ion such as an alkali metal, alkaline earth metal, or ammonium counterion. This list of counterions, however, is non-limiting.

The expression "one or more" means "at least one" and thus includes individual components as well as mixtures/combinations.

Other than in the operating examples, or where otherwise indicated, all numbers expressing quantities of ingredients and/or reaction conditions are to be understood as being modified in all instances by the term "about," meaning within +/−5% of the indicated number.

All percentages, parts and ratios herein are based upon the total weight of the compositions of the present invention, unless otherwise indicated.

"Keratinous substrates" as used herein, includes, but is not limited to keratin fibers such as hair on the human head.

"Conditioning" as used herein means imparting to one or more hair fibers at least one property chosen from combability, moisture-retentivity, luster, shine, and/or softness. The state of conditioning can be evaluated by any means known in the art, such as, for example, measuring, and comparing, the ease of combability of the treated hair and of the untreated hair in terms of combing work (gm-in), and consumer perception.

The term "stable" as used herein means that the composition does not exhibit phase separation and/or crystallization for a period of time, for example, for at least 1 day (24 hours), one week, one month, or one year.

"Volatile", as used herein, means having a flash point of less than about 100° C.

"Non-volatile", as used herein, means having a flash point of greater than about 100° C.

As used herein, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc. All ranges and values disclosed herein are inclusive and combinable. For examples, any value or point described herein that falls within a range described herein can serve as a minimum or maximum value to derive a sub-range, etc.

The term "substantially free" or "essentially free" as used herein means that there is less than about 5% by weight of a specific material added to a composition, based on the total weight of the compositions. Nonetheless, the compositions may include less than about 3%, less than about 2%, less than about 1%, less than about 0.5%, less than about 0.1%, or none of the specified material.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The examples that follow serve to illustrate embodiments of the present disclosure without, however, being limiting in nature. It will be apparent to those skilled in the art that various modifications and variations can be made in the delivery system, compositions, and methods of the invention without departing from the spirit or scope of the invention.

EXAMPLES

Implementation of various non-limiting embodiments of the disclosure is demonstrated by way of the following examples.

Example 1—Hair Color Compositions

The following hair color compositions according to the disclosure were prepared.

| INCI | Example 1A | Example 1B |
|---|---|---|
| BEHENTRIMONIUM CHLORIDE | 2.6 | 2.6 |
| AMODIMETHICONE (and) TRIDECETH-6 (and) CETRIMONIUM CHLORIDE | 2 | 2 |
| 2-OLEAMIDO-1,3-OCTADECANEDIOL | 0.01 | 0.01 |
| GUAR HYDROXYPROPYLTRIMONIUM CHLORIDE | 0.1 | 0.1 |
| FATTY ALCOHOL (CETEARYL ALCOHOL and CETYL ALCOHOL) | 4.75 | 4.75 |
| HYDROXYETHYLCELLULOSE | 0.2 | 0.2 |
| TAURINE | 2 | 3 |
| CITRIC ACID | 2.28 | 3 |
| ETHANOLAMINE | 0.5 | 0.5 |
| HAIR COLORING AGENTS | 1.274 | 1.274 |
| PRESERVATIVE | 0.04 | 0.04 |
| SOLVENT (WATER and C12-15 ALKYL BENZOATE) | QS | QS |

The compositions of Examples 1A and 1B were prepared by melting the fatty alcohol compounds in water at 95° C. Separately, citric acid, behentrimonium chloride and dyes were solubilized in hot water at 90° C. then mixed at 70° C. The remaining components (other than the preservative) were added and stirred, then the pre-melted fatty alcohol compound mixture was added and the heat was discontinued. An emulsion formed after approximately 10 minutes of stirring. The mixture was subjected to a cold water bath, the preservative was added along with any remaining dyes and additional water, and the pH of the composition was adjusted to 3.5+/−0.2 when the temperature was approximately 25° C.

Example 2—Comparative Hair Color Composition

The following comparative hair color composition was prepared in the same manner as described in Example 1.

| INCI | Example 2 |
|---|---|
| BEHENTRIMONIUM CHLORIDE | 2.6 |
| AMODIMETHICONE (and) TRIDECETH-6 (and) CETRIMONIUM CHLORIDE | 2 |
| 2-OLEAMIDO-1,3-OCTADECANEDIOL | 0.01 |
| GUAR HYDROXYPROPYLTRIMONIUM CHLORIDE | 0.1 |
| FATTY ALCOHOL (CETEARYL ALCOHOL and CETYL ALCOHOL) | 4.75 |
| HYDROXYETHYLCELLULOSE | 0.2 |
| TAURINE | — |
| CITRIC ACID | 0.025 |
| ETHANOLAMINE | — |
| HAIR COLORING AGENTS | 1.274 |
| PRESERVATIVE | 0.04 |
| SOLVENT (WATER and C12-15 ALKYL BENZOATE) | QS |

Example 3—Evaluation of Strength of Hair

Four separate swatches of hair were bleached two times with Flashlift bleach, mixed 1:2 with 30V developer, then washed and rinsed after a leave-in period of 50 minutes. One swatch was then colored with the composition of Example 1A, one swatch was colored with the composition of Example 1 B, and one swatch was colored with the comparative composition of Example 2, and the three colored swatches were subsequently rinsed, washed, and rinsed again after a leave-in period of 20 minutes.

In order to determine the impact on strength of hair colored with the inventive compositions, wet tensile strength of all four swatches was evaluated using a fiber tensile testing instrument from Dia-Stron known as an MTT (Miniature Tensile Tester). From the test, Young's Modulus (elasticity, MPa) and Break Stress (force per unit area required to break the fiber, MPa) were determined.

As seen in FIG. 1, while the swatch colored with the comparative composition of Example 2 (B) provides some minimal improvement in Break Stress relative to the bleach-only swatch (A), the swatch colored with the composition of Example 1B (D) provides improvement relative to both swatches (A) and (B), and the swatch colored with the composition of Example 1A (C) provides even greater improvement.

Figure 2:
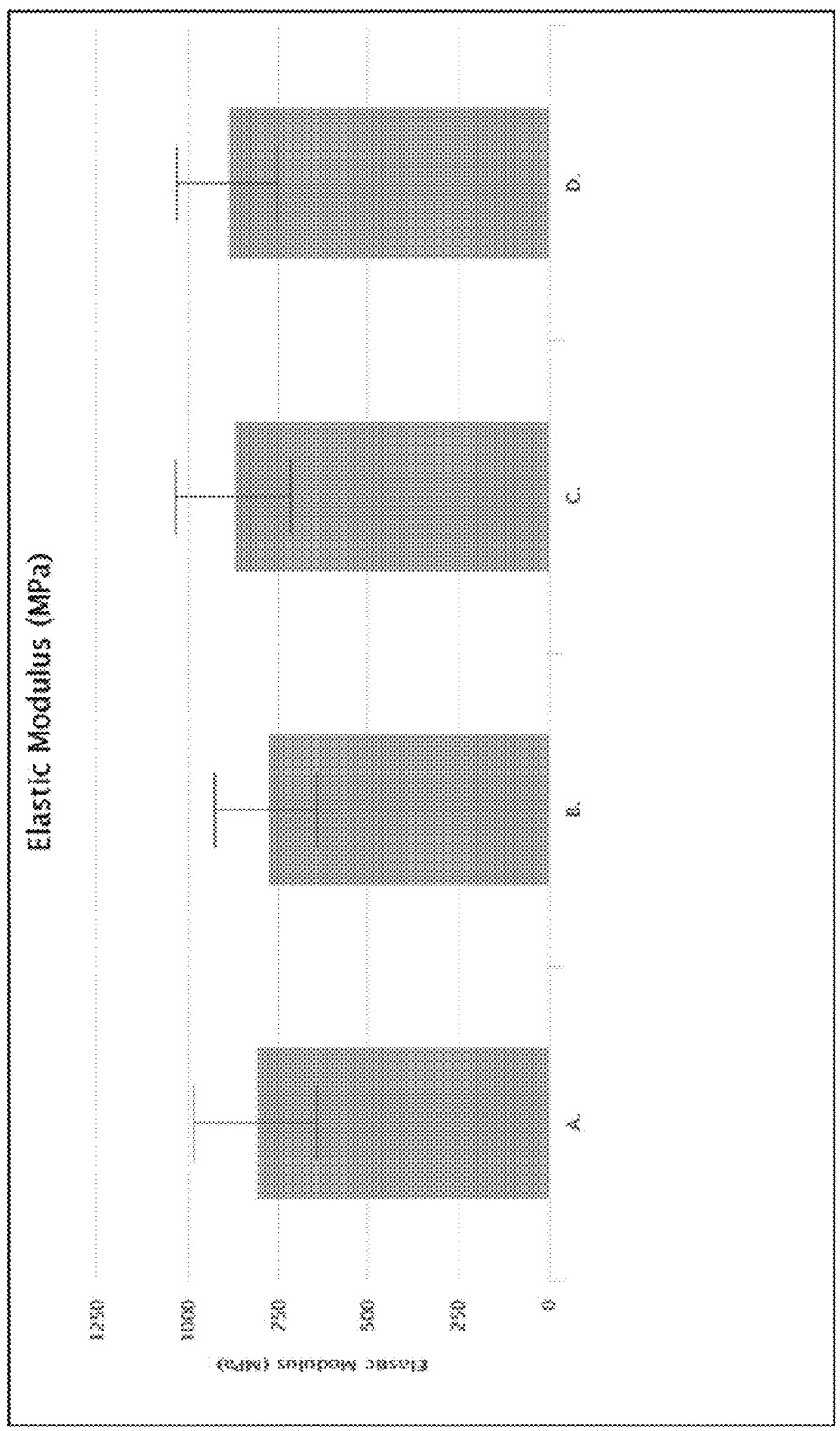
FIG. 2 is a comparison of Elastic Modulus of hair.

As seen in FIG. 2, the swatch colored with the comparative composition of Example 2 (B) results in poorer Elastic Modulus than the bleach-only swatch (A), while both the swatch colored with the composition of Example 1A (C) and the composition of Example 1B (D) provide improvement relative to both swatches (A) and (B).

Based on the MTT results, therefore, it is evident that the addition of a combination of an amino acid, a carboxylic acid, and an amine to hair coloring compositions provides a statistically significant improvement in Elastic Modulus and Break Stress compared to bleach alone, as well as to a hair color composition not comprising the combination. The results in FIGS. 1 and 2 thus demonstrate that the inventive combination of amino acid, carboxylic acid, and optionally an amine provides improved strength and resistance to breakage to hair treated with a hair color composition comprising the combination.

Example 4—Stability Testing of Hair Color Compositions

The following formulation of Example 4 was prepared in the same manner as described in Example 1, and pH adjusted to a pH of 3.5+/−0.3.

| INCI | Example 4 |
| --- | --- |
| BEHENTRIMONIUM CHLORIDE | 2.054 |
| AMODIMETHICONE (and) TRIDECETH-6 (and) CETRIMONIUM CHLORIDE | 1.26 |
| 2-OLEAMIDO-1,3-OCTADECANEDIOL | 0.01 |
| GUAR HYDROXYPROPYLTRIMONIUM CHLORIDE | 0.1 |
| FATTY ALCOHOL (CETEARYL ALCOHOL and CETYL ALCOHOL) | 4.75 |
| HYDROXYETHYLCELLULOSE | 0.2 |
| TAURINE | 2.0 |
| CARBOXYLIC ACID (CITRIC ACID and FUMARIC ACID) | 2.282 |
| HAIR COLORING AGENTS | 1.274 |
| PRESERVATIVE | 0.2 |
| SOLVENT (WATER and C12-15 ALKYL BENZOATE) | QS |

The formulation of Example 4 formed a black cream. The stability of the formulation was evaluated by storing different samples of the formulation at room temperature (RT, 25° C.), 45° C., and 4° C. for eight (8) weeks, and then evaluating both pH and performance.

At time 0 (T=0) the pH was measured and the Example 4 composition, as well as a Standard (freshly made standard formula) and Example 2, was applied to platinum hair swatches (20 minutes and rinsed, washed, and rinsed again). Result at T=0: Example 4 color results matched that of freshly made Standard, and also matched the result of Example 2.

After eight (8) weeks, the pH of each sample was evaluated, and each sample was applied to platinum hair swatches (20 minutes and rinsed, washed, and rinsed again). After eight (8) weeks, the pH of each sample was in the range of 3.8-4, and the swatches each had an even black color deposition, as shown in the below table:

| | pH | Color |
| --- | --- | --- |
| 25° C. | 3.94 | Black |
| 45° C. | 3.83 | Black |
| 4° C. | 3.82 | Black |

As demonstrated in Example 4, the formulation at 25° C., 45° C. and 4° C. exhibited satisfactory pH stability over eight (8) weeks, and evaluation of the treated hair swatches showed that an even black color was maintained, without color shift. At T=8 weeks: pH was measured, showed stability of composition over time at varying temperatures; and swatches color result at T=8 was found to remain/no color shift. Example 4 illustrates that the hair color compositions according to the disclosure remain stable and provide uniform coverage with no color shift over an extended period of time, even at varying temperatures, which is important for hair strength and satisfactory color of the hair.

Example 5—Hair Color Compositions

The following hair color compositions were prepared in the same manner as described in Example 1.

| | Example | | | | | |
| --- | --- | --- | --- | --- | --- | --- |
| INCI | 5A | 5B | 5C | 5D | 5E | 5F |
| BEHENTRIMONIUM CHLORIDE | 2.6 | 2.6 | 2.6 | 2.6 | 2.6 | 2.6 |
| AMODIMETHICONE (and) TRIDECETH-6 (and) CETRIMONIUM CHLORIDE | 2.0 | 2.0 | 2.0 | 2.0 | 2.0 | 2.0 |
| 2-OLEAMIDO-1,3-OCTADECANEDIOL | 0.01 | 0.01 | 0.01 | 0.01 | 0.01 | 0.01 |
| GUAR HYDROXYPROPYL-TRIMONIUM CHLORIDE | 0.1 | 0.1 | 0.1 | 0.1 | 0.1 | 0.1 |
| FATTY ALCOHOL (CETYL ALCOHOL and CETEARYL ALCOHOL) | 4.75 | 4.75 | 4.75 | 4.75 | 4.75 | 4.75 |
| HYDROXYETHYL-CELLULOSE | 0.2 | 0.2 | 0.2 | 0.2 | 0.2 | 0.2 |
| TAURINE | 1.0 | 1.0 | 1.0 | 1.0 | 1.0 | 1.0 |
| CITRIC ACID | 1.025 | 1.17 | 1.17 | 1.17 | 1.17 | 1.17 |
| ETHANOLAMINE | 0.2 | 0.1 | 0.1 | 0.1 | 0.1 | 0.1 |
| HAIR COLORING AGENTS | 1.274 | 0.05 | 0.1 | 0.4 | 0.8 | 0.8 |
| PRESERVATIVE | 0.2 | 0.2 | 0.2 | 0.2 | 0.2 | 0.2 |
| SOLVENT (WATER and C12-15 ALKYL BENZOATE) | QS | QS | QS | QS | QS | QS |

Example 6—Evaluation of Color Shift and Deposition

Two separate swatches of hair were bleached two times with Flashlift bleach, mixed 1:2 with 30V developer, then washed and rinsed after a leave-in period of 50 minutes. One swatch was then colored with the composition of Example 5A, and one swatch was colored with the comparative composition of Example 2, and the colored swatches were subsequently rinsed, washed, and rinsed again after a leave-in period of 20 minutes.

A visual examination of the two swatches confirmed that the color deposition of the composition of Example 5A was more uniform and even, with no color shift, compared to the color deposition of the composition of Example 2. This demonstrates that the addition of a combination of an amino acid, a carboxylic acid, and optionally an amine to hair coloring compositions provides no shift in color and more uniform and even deposition as compared to conventional direct dye compositions, and Example 2.

Example 7—Gel Hair Color Compositions

The following gel hair color compositions, all of which had a pH in the range of about 3.5 to about 4, were prepared in the same manner as described in Example 1.

|  | Example | | | | |
|---|---|---|---|---|---|
| INCI | Example 8A | Example 8B | Example 8C | Example 8D | Example 8E |
| BEHENTRIMONIUM CHLORIDE | 2.054 | 2.054 | 2.054 | 2.054 | — |
| AMODIMETHICONE (and) TRIDECETH-6 (and) CETRIMONIUM CHLORIDE | 1.26 | 1.26 | 1.26 | 1.26 | — |
| 2-OLEAMIDO-1,3-OCTADECANEDIOL | 0.01 | 0.01 | 0.01 | 0.01 | — |
| GUAR HYDROXYPROPYL-TRIMONIUM CHLORIDE | 0.09825 | 0.09825 | 0.09825 | 0.09825 | — |
| FATTY ALCOHOL (CETEARYL ALCOHOL and CETYL ALCOHOL) | 4.75 | 4.75 | 4.75 | 4.75 | — |
| THICKENER | 0.2 | 0.2 | 0.2 | 0.2 | 0.392 |
| TAURINE | 2.0 | 2.0 | 3.0 | 3.0 | 3.0 |
| CARBOXYLIC ACID (CITRIC ACID and FUMARIC ACID) | 2.282 | 2.282 | 3.02 | 3.02 | — |
| CARBOXYLIC ACID (CITRIC ACID) | — | — | — | — | 3.0 |
| ETHANOLAMINE | — | 0.5 | — | 0.5 | 0.5 |
| HAIR COLORING AGENTS | 1.274 | 1.274 | 1.274 | 1.274 | 1.274 |
| PRESERVATIVE | 0.04 | 0.04 | 0.04 | 0.04 | — |
| SOLVENT (WATER, ISOPROPYL ALCOHOL, and C12-15 ALKYL BENZOATE) | QS | QS | QS | QS | — |
| SOLVENT (WATER) | — | — | — | — | QS |

The above examples demonstrate that the formulations according to the disclosure unexpectedly provide improved strength, smoothness, and feel to the hair, while achieving stability and superior evenness and uniformity of color deposit.

The invention claimed is:

1. A hair color composition comprising:
   (a) at least one amino acid comprising taurine,
   (b) at least one carboxylic acid,
   (c) at least one amine, and
   (d) at least one hair coloring agent chosen from direct dyes and pigments,
   wherein the at least one amine is present in an amount ranging from about 0.01% to about 5% by weight, relative to the total weight of the composition, and
   wherein the composition has a pH ranging from about 2 to less than 7.

2. The hair color composition according to claim 1, wherein the at least one amino acid is present in the composition in an amount ranging from about 0.2% to about 5% by weight, relative to the total weight of the composition.

3. The hair color composition according to claim 1, wherein the at least one carboxylic acid is chosen from oxalic acid, malonic acid, glutaric acid, succinic acid, adipic acid, glycolic acid, citric acid, tartaric acid, malic acid, sebacic acid, maleic acid, fumaric acid, benzoic acid, citraconic acid, aconitic acid, propane-1,2,3-tricarboxylic acid, trimesic acid, or combinations thereof.

4. The hair color composition according to claim 1, wherein the at least one carboxylic acid is present in the composition in an amount ranging from about 0.2% to about 5% by weight, relative to the weight of the composition.

5. The hair color composition according to claim 1, wherein the at least one carboxylic acid and the at least one amino acid are present in a ratio of about 1:1.

6. The hair color composition according to claim 1, further comprising at least one fatty alcohol.

7. The hair color composition according to claim 1, further comprising at least one surfactant.

8. The hair color composition according to claim 1, further comprising at least one thickening agent.

9. The hair coloring composition according to claim 1, further comprising at least one solvent chosen from water, glycols, alcohols, or mixtures thereof.

10. A method for altering the color of the hair, comprising applying to the hair a composition comprising:
    (a) at least one amino acid comprising taurine,
    (b) at least one carboxylic acid,
    (c) at least one amine, and
    (d) at least one hair coloring agent chosen from direct dyes and pigments,
    wherein the at least one amine is present in an amount ranging from about 0.01% to about 5% by weight, relative to the total weight of the composition, and
    wherein the composition has a pH ranging from about 2 to less than 7.

11. The method according to claim 10, wherein the at least one amino acid is chosen from taurine, alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine, or combinations thereof.

12. The method according to claim 10, wherein the at least one amino acid is present in the composition in an amount ranging from about 0.2% to about 5% by weight, relative to the weight of the hair color composition.

13. The method according to claim 10, wherein the at least one carboxylic acid is chosen from oxalic acid, malonic acid, glutaric acid, succinic acid, adipic acid, glycolic acid, citric acid, tartaric acid, malic acid, sebacic acid, maleic acid, fumaric acid, benzoic acid, citraconic acid, aconitic acid, propane-1,2,3-tricarboxylic acid, trimesic acid, or combinations thereof.

14. The method according to claim 10, wherein the at least one carboxylic acid is present in the composition in an amount ranging from about 0.2% to about 5% by weight, relative to the weight of the hair color composition.

15. The method according to claim 10, wherein the at least one carboxylic acid and the at least one amino acid are present in the composition in a ratio of about 1:1.

16. The method according to claim 10, wherein the composition comprises from about 0.01% up to about 5% of at least one amine.

17. The method according to claim 10, wherein the composition further comprises at least one solvent and at least one additional component chosen from fatty alcohols, surfactants, and thickening agents.

18. The method according to claim 10, further comprising a step of washing and/or rinsing the hair after a leave-in period ranging from about 3 minutes to about 45 minutes.

19. A hair color composition comprising:
   (a) from about 0.2% to about 5% of taurine,
   (b) from about 0.2% to about 5% of citric acid,
   (c) from about 0.01% to about 5% of at least one amine,
   (d) at least one cationic surfactant,
   (e) at least one fatty alcohol, and
   (f) at least one hair coloring agent selected from direct dyes,
   wherein the composition has a pH ranging from about 3 to about 4, and
   wherein all of the percentages are by weight, relative to the total weight of the hair color composition.

* * * * *